US012704504B2

(12) United States Patent
Huber et al.

(10) Patent No.: US 12,704,504 B2

(45) Date of Patent: Aug. 11, 2026

(54) DERIVATIZATION OF BETA-LACTAM ANTIBIOTICS AS CALIBRATORS/ISTD IN MASSSPEC MEASUREMENTS

(71) Applicant: Roche Diagnostics Operations, Inc., Indianapolis, IN (US)

(72) Inventors: Florian Huber, Penzberg (DE); Thomas Scheidt, Penzberg (DE); Gaston Hubertus Maria Vondenhoff, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1114 days.

(21) Appl. No.: 17/745,367

(22) Filed: May 16, 2022

(65) Prior Publication Data

US 2022/0365077 A1 Nov. 17, 2022

Related U.S. Application Data

(63) Continuation of application No. PCT/EP2020/081819, filed on Nov. 12, 2020.

(30) Foreign Application Priority Data

Nov. 15, 2019 (EP) .................................... 19209520

(51) Int. Cl.
*G01N 33/534* (2006.01)
*H01J 49/00* (2006.01)

(52) U.S. Cl.
CPC ........ *G01N 33/534* (2013.01); *H01J 49/0009* (2013.01)

(58) Field of Classification Search
None
See application file for complete search history.

(56) References Cited

U.S. PATENT DOCUMENTS

| | | | | |
|---|---|---|---|---|
| 4,316,882 A * | 2/1982 | Levine | A61K 31/43 514/192 |
| 2014/0220086 A1 | 8/2014 | Altman et al. | |
| 2014/0243241 A1 | 8/2014 | Brans et al. | |

FOREIGN PATENT DOCUMENTS

| | | | |
|---|---|---|---|
| EP | 0113965 A2 | 7/1984 |
| ES | 2197811 A1 | 1/2004 |
| JP | 2016039814 A | 3/2016 |
| WO | 2011154517 A1 | 12/2011 |
| WO | 2021094410 A1 | 5/2021 |

OTHER PUBLICATIONS

Deshpande. Current Science, 2004, 87 (12), 1684-1695 (Year: 2004).*
Coates. British Journal of Pharmacology, 2011, 163, 184-194 (Year: 2011).*
Pagano. The Journal of Antibiotics, 2011, 64, 673-677) (Year: 2011).*
Viola. European Journal of Pharmaceutical Sciences, 2019, 136, 104957, 1-9, available online Jun. 14, 2019 (Year: 2019).*
Meng. The Journal of Immunology, 2017, 198 (11), 4217-4227; The Journal of Immunology, 2018, 200 (5), 1952 (Year: 2017).*
Wang. Rapid Communications in Mass Spectrometry, 2019, 33, 1410-1419, available online May 30, 2019 (Year: 2019).*
Kessler. Journal of the Chemical Society, Perkin Transactions 2, 1983, 11, 1699-1703 (Year: 1983).*
De Rosa et el., Novel Penicillin-Type Analogues Bearing a Variable Substituted 2-Azetidinone Ring at Position 6: Synthesis and Biological Evaluation, Molecules, vol. 20, 2015, pp. 22044-22057.
Japanese Patent Office, Office Action issued in corresponding Application No. 2022-527697, dated Nov. 5, 2024, 8 pp.
The International Bureau of WIPO, International Preliminary Report on Patentability issued in corresponding Application No. PCT/EP2020/081819, dated May 17, 2022, 7 pp.
International Search Report; European Patent Office; International Application No. PCT/EP2020/081819; Mar. 25, 2021; 6 pages.
Written Opinion of the International Searching Authority; European Patent Office; International Application No. PCT/EP2020/081819; Mar. 25, 2021; 8 pages.
Van Holthoon, Frédérique et al., Quantitative analysis of penicillins in porcine tissues, milk and animal feed using derivatisation with piperidine and stable isotope dilution liquid chromatography tandem mass spectrometry, Anal Bioanal Chem, 2010, pp. 3027-3040, vol. 396.
Llinás, Antonio et al., Intramolecular general acid catalysis in the aminolysis of β-lactam antibiotics, Org. Biomol. Chem. 2004, pp. 651-654, vol. 2.
Llinás, Antonio et al., Thiol-catalysed hydrolysis of benzylpenicillin, Journal of the Chemical Society, Perkin Trans 2, 2000, pp. 1521-1525.
D'Cunha, Ronilda et al., Quantification of Cefepime, Meropenem, Piperacillin, and Tazobactam in Human Plasma Using a Sensitive and Robust Liquid Chromatography—Tandem Mass Spectrometry Method, Part 1: Assay Development and Validation, Antimicrobial Agents and Chemotherapy, 2018, 15 pp., vol. 62, No. 9.
Zander, Johannes et al., Effects of biobanking conditions on six antibiotic substances in human serum assessed by a novel evaluation protocol, Clinical Chemistry and Laboratory Medicine, 2016, pp. 265-274, vol. 54, No. 2.
Wiedemann, Elija N. et al., Kinetic and Theoretical Studies of Beta-Lactone Reactivity—A Quantitative Scale for Biological Application, ChemPlusChem, 2015, pp. 1673-1679, vol. 80.
Korean Office Action; Korean Intellectual Property Office; Korean Patent Application No. 10-2022-7016809; May 28, 2025; 8 pages.

* cited by examiner

*Primary Examiner* — Noble E Jarrell

(74) *Attorney, Agent, or Firm* — Taft Stettinius & Hollister LLP

(57) ABSTRACT

The invention relates to a complex comprising an antibiotic substance and a nucleophilic derivatization reagent, compositions comprising the complex, kits comprising complex or composition, as well as uses of the complex or composition.

17 Claims, 11 Drawing Sheets

Figure 1:
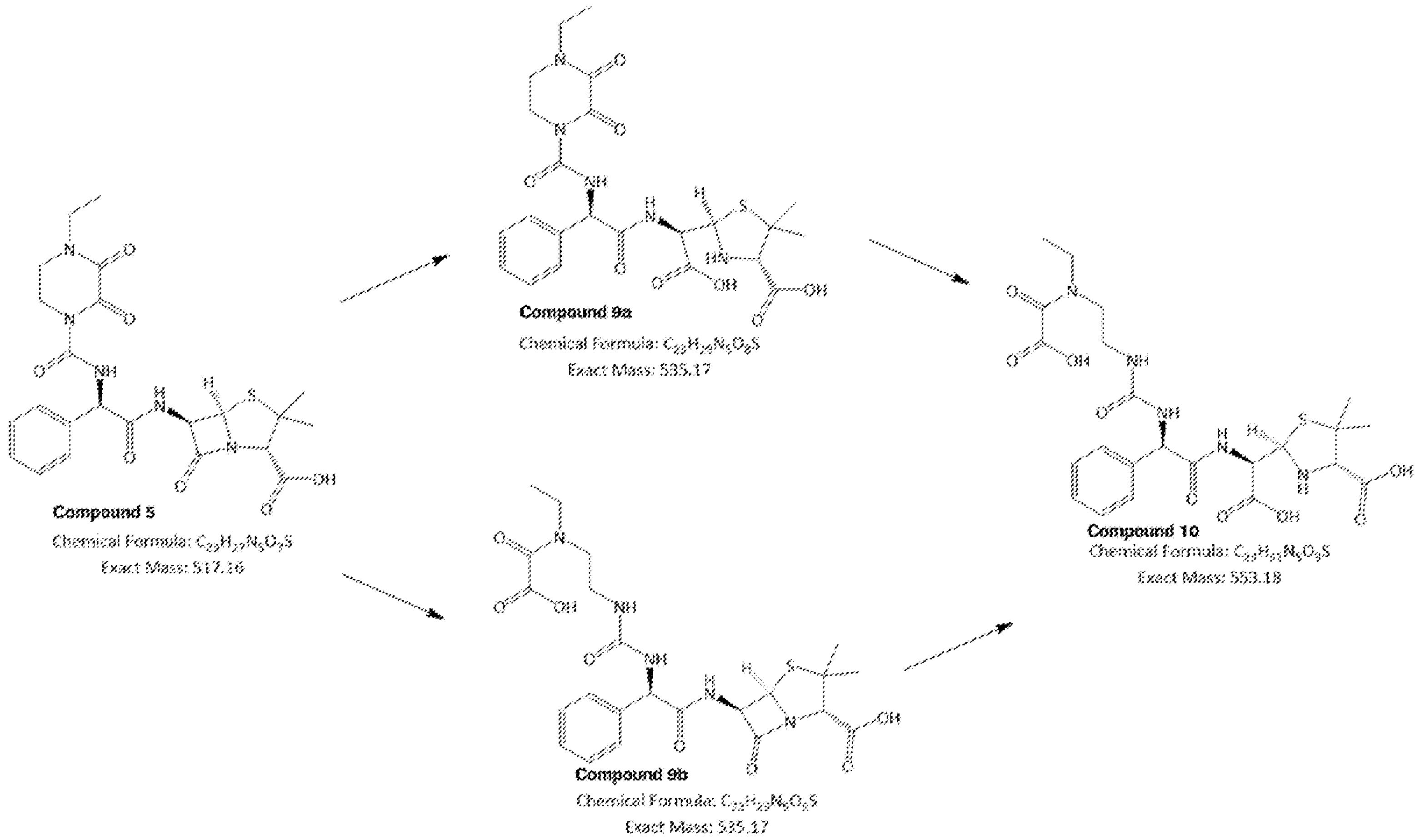

Compound 5
Chemical Formula: $C_{23}H_{27}N_5O_7S$
Exact Mass: 517.16

Compound 9a
Chemical Formula: $C_{23}H_{29}N_5O_8S$
Exact Mass: 535.17

Compound 9b
Chemical Formula: $C_{23}H_{29}N_5O_8S$
Exact Mass: 535.17

Compound 10
Chemical Formula: $C_{23}H_{31}N_5O_9S$
Exact Mass: 553.18

A

Compound 1

Chemical Formula: $C_{17}H_{25}N_3O_5S$
Exact Mass: 383.15

Compound 2

Chemical Formula: $C_{20}H_{34}N_4O_5S$
Exact Mass: 442.22

B

Compound 1

Chemical Formula: $C_{17}H_{25}N_3O_5S$
Exact Mass: 383.15

Compound 3

Chemical Formula: $C_{21}H_{36}N_4O_5S$
Exact Mass: 456.24

C

Compound 1

Chemical Formula: $C_{17}H_{25}N_3O_5S$
Exact Mass: 383.15

Compound 4

Chemical Formula: $C_{22}H_{38}N_4O_5S$
Exact Mass: 470.26

A

Compound 5

Chemical Formula: $C_{23}H_{27}N_5O_7S$
Exact Mass: 517.16

Compound 6

Chemical Formula: $C_{29}H_{45}N_7O_7S$
Exact Mass: 635.31

B

Compound 5

Chemical Formula: $C_{23}H_{27}N_5O_7S$
Exact Mass: 517.16

Compound 7

Chemical Formula: $C_{31}H_{49}N_7O_7S$
Exact Mass: 663.34

C

Compound 5

Chemical Formula: $C_{23}H_{27}N_5O_7S$
Exact Mass: 517.16

Compound 8

Chemical Formula: $C_{33}H_{53}N_7O_7S$
Exact Mass: 691.37

Compound 11

Chemical Formula: $C_{27}H_{33}D_5N_6O_7S$

Exact Mass: 595.28

Component Name

- Compound 3, MRM 1
- Compound 3, MRM 2
- Compound 3, MRM 3
- Compound 4, MRM 1
- Compound 4, MRM 2
- Compound 4, MRM 3
- Compound 2, MRM 1
- Compound 2, MRM 2
- Compound 2, MRM 3

Component Name
- Compound 7, MRM 1
- Compound 7, MRM 2
- Compound 7, MRM 3
- Compound 8, MRM 1
- Compound 8, MRM 2
- Compound 8, MRM 3
- Compound 6, MRM 1
- Compound 6, MRM 2
- Compound 6, MRM 3

DERIVATIZATION OF BETA-LACTAM ANTIBIOTICS AS CALIBRATORS/ISTD IN MASSSPEC MEASUREMENTS

CROSS-REFERENCE TO RELATED APPLICATIONS

This application is a continuation of International PCT Application No. PCT/EP2020/081819 filed on Nov. 12, 2020, which claims priority to European Patent Application No. 19209520.6 filed on Nov. 15, 2019, the contents of each application are incorporated herein by reference in their entireties.

MEASUREMENTS

The invention relates to a complex formed of an antibiotic substance and a nucleophilic derivatization reagent, compositions comprising the complex, kits comprising complex or composition, as well as uses of the complex or composition.

BACKGROUND

β-Lactam antibiotics are a class of antibiotics that are prescribed most commonly as either specific or broad-spectrum antibiotics for patients infected with bacteria. This class of antibiotics works by interfering with the crosslinking of the peptidoglycan layer that is most dominant in Gram-positive bacteria. They exhibit a bacteriocidal effect which is concentration dependent. Therefore, it is critical to keep the antibiotic concentration above the MIC. However, higher concentrations lead to adverse effects. Moreover, it has been reported that the pharmacokinetics of these compounds is highly variable and therefore unpredictable (Ronilda D'Cunha et al.; 2018; Antimicrobial Agents and Chemotherapy 62 (9)).

The mechanism of action of these antibiotics is by reacting the four-membered 3-lactam ring with the D-alanyl-D-alanyl-transpeptidase, thereby inhibiting the formation of cross-links between the peptidoglycan polymers of the outer cell-wall.

Thus, the relative instable lactam moiety is responsible for the mechanism of action of these antibiotics. However, this instability also leads to a partial hydrolyzation of these compounds upon dissolution in protic solvents. Even more so, hydrolyzation is naturally further catalyzed by the presence of acid or base and enhanced with elevated temperatures. Obviously, hydrolyzed antibiotics are no longer active compounds that can inhibit bacterial growth. The term "hydrolyzation" and the term "hydrolysis" can be used interchangeable here in the disclosure. The term "hydrolysis" is known for a skilled person and thus not explained in detail.

Therapeutic Drug Monitoring (TDM) is a field of medicine that aims to quantify drugs from human sample material with the aim to monitor drug concentrations in the body. As hydrolyzation continues after patient sampling (e.g. blood collection), it is impossible to obtain accurate concentrations of the native β-Lactam antibiotics. Considerable efforts have been made to study and address β-Lactam instability in the field of Therapeutic Drug Monitoring (TDM), mostly focusing storage conditions that aim to retain the compounds in their native (i.e. unhydrolyzed) form (Zander et al.; 2016; Clinical Chemistry And Laboratory Medicine; 54(2)).

Since it is crucial to carefully monitor antibiotic concentrations, a valid and stable method to quantify these compounds from human and animal matrices is required. Currently, quantitation of these antibiotics may be performed by LC-MS/MS. For this method it is pivotal to calibrate the system using the antibiotics of interest as calibrator. Most commonly an isotopically labeled internal standard (ISTD) with a known concentration is used to account for analyte losses that occur in handling/purification of the compound before it is measured by MS. The ISTD also corrects for deviations in ionization of the different samples. Hence, a prerequisite for this method is that the concentrations of both calibrators and ISTDs are known. Since hydrolyzation of these compounds already occurs under very mild conditions (Wiedemann et al.; 2015; ChemPlusChem, 80), it is difficult to keep these calibrators and ISTD intact up to the point when they are used in measurements. This leads to deviations of the calibrator and ISTD concentrations and implies that exact quantitation of the analyte of interest in the patient sample is not possible. There is thus, an urgent need for stable calibrators and ISTDs to be able to measure β-Lactam antibiotic levels without hampering the accuracy of measurement caused by instable ISTDs and calibrators.

Here for the first time, we were able to show that 3-lactam antibiotics can be stabilized in order to serve as stable calibrators and ISTDs ensuring accurate sample measurements.

SUMMARY OF THE INVENTION

In a first aspect, the present invention relates to a complex formed of an antibiotic substance and a nucleophilic derivatization reagent.

In a second aspect, the present invention relates to a composition comprising the complex of the first aspect.

In a third aspect, the present invention relates to a kit comprising a) the complex of the first aspect or the composition of the second aspect, and b) a package insert.

In a fourth aspect, the present invention relates to the use of a complex of the first aspect or the composition of the second aspect for Mass Spec measurements.

In a fifth aspect, the present invention relates to the use of a nucleophilic derivatization reagent to stabilize an antibiotic substance, in particular to be suitable as ISTD and/or calibrator in MassSpec Measurements.

In a sixth aspect, the present invention relates to a derivatized antibiotic substance suitable as ISTD and/or calibrator in MassSpec Measurements.

In a seventh aspect, the present invention relates to the use of derivatized antibiotic as ISTD and/or calibrator in Mass Spec Measurements.

In an eighth aspect, the present invention relates to a method of producing a stabilized antibiotic substance, comprising derivatizing an antibiotic substance with a nucleophilic derivatization reagent.

LIST OF FIGURES

FIG. 1: Schematic drawing of hydrolyzation pathway of Piperacillin (compound 5).

Figure 2:
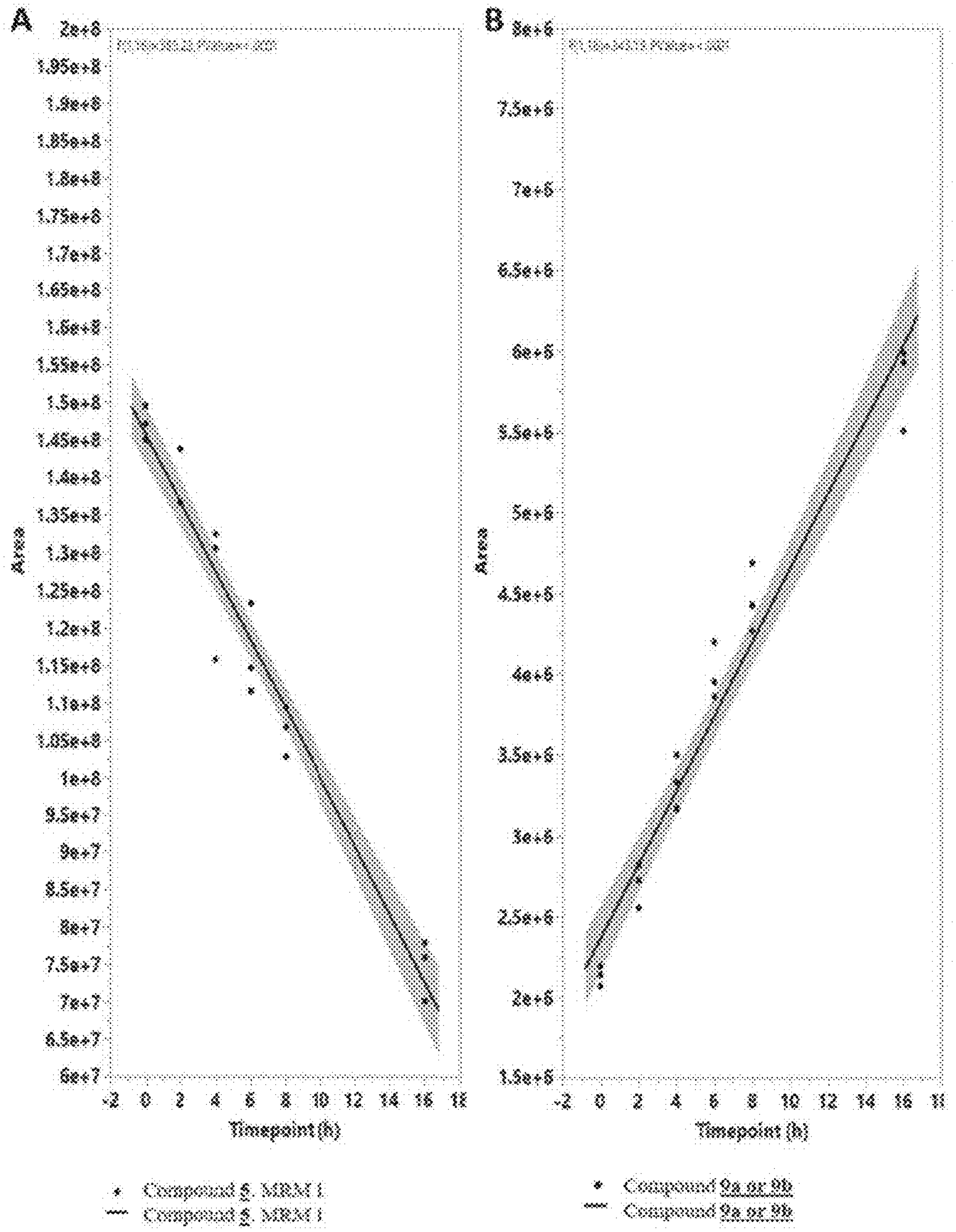

FIG. 2: Measured peak area over 16 h of A) native Piperacillin (compound 5); and B) single hydrolyzed Piperacillin (compound 9a or 9b, FIG. 1) in water at room temperature. Depicted with confidence fit and F-test. For clarity, reference lines have been drawn through the average area values.

Figure 3:
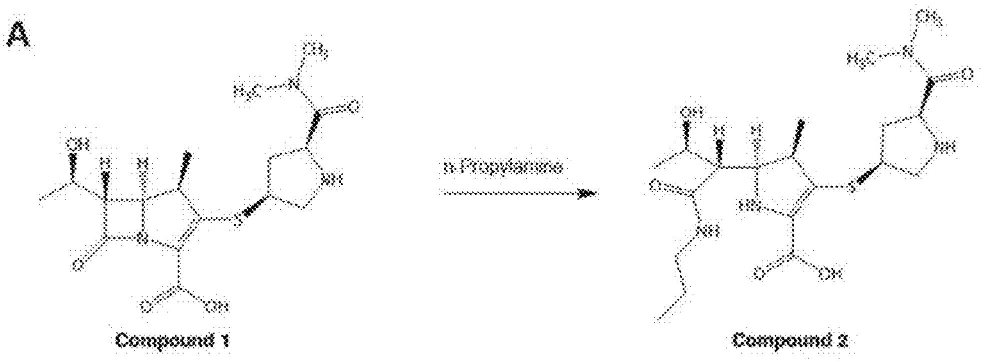
Figure 3:
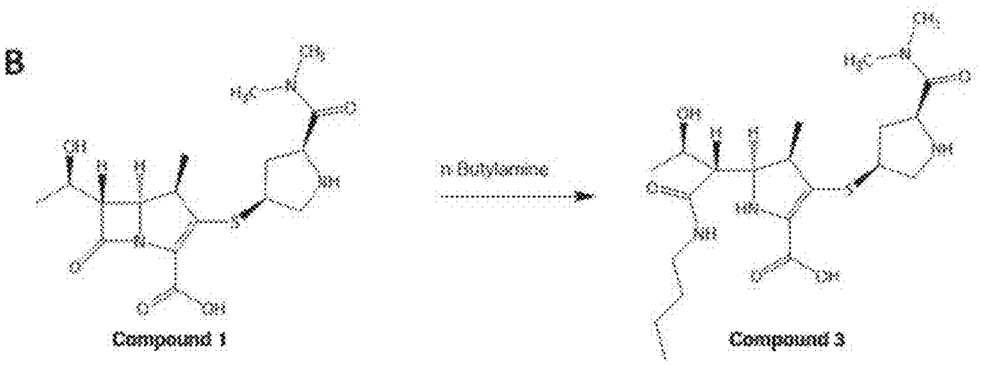
Figure 3:
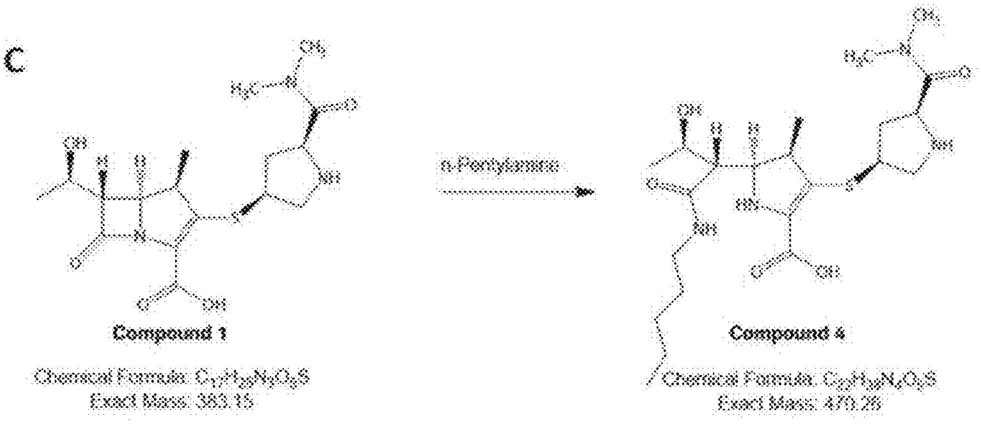

FIG. 3: Schematic drawing of the derivatization reaction sequence of Meropenem (compound 1) with different reagents: A) propylamine; B) butylamine, C) pentylamine FIG. 4. Schematic drawing of the derivatization reaction sequence of Piperacillin (compound 5) with different reagents: A) propylamine; B) butylamine, C) pentylamine FIG. 5: Measured peak area over 16 h of double-derivatized Piperacillin (compound 7) in water at room temperature, for two MRM transitions. Depicted with confidence fit and F-test. For clarity, reference lines have been drawn through the average area values.

Figure 6:
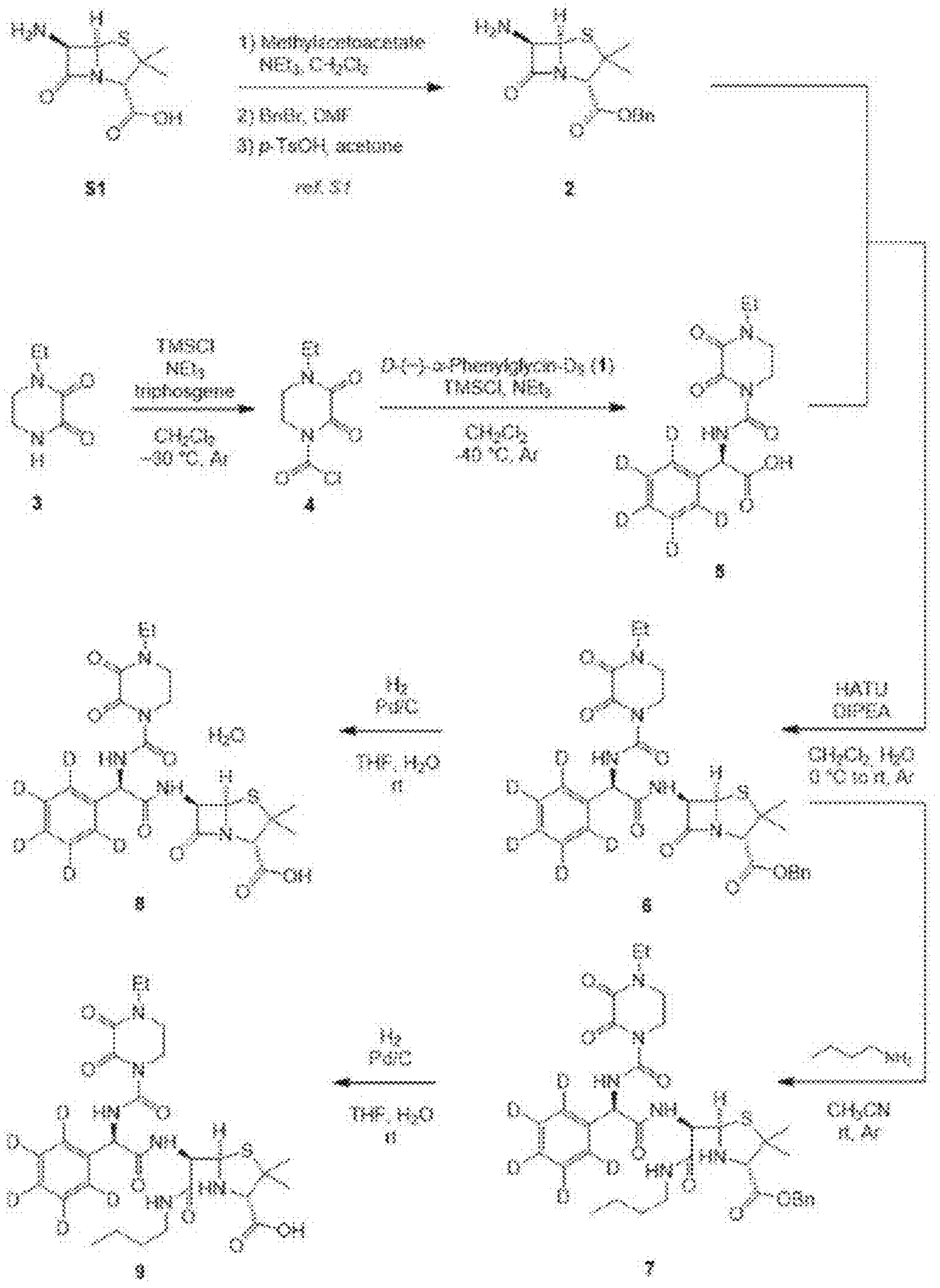

FIG. 6: Synthesis routes for Piperacillin-$D_5$ monohydrate (8) and Piperacillin-n-butylamide-$D_5$ (9)

Figure 7:
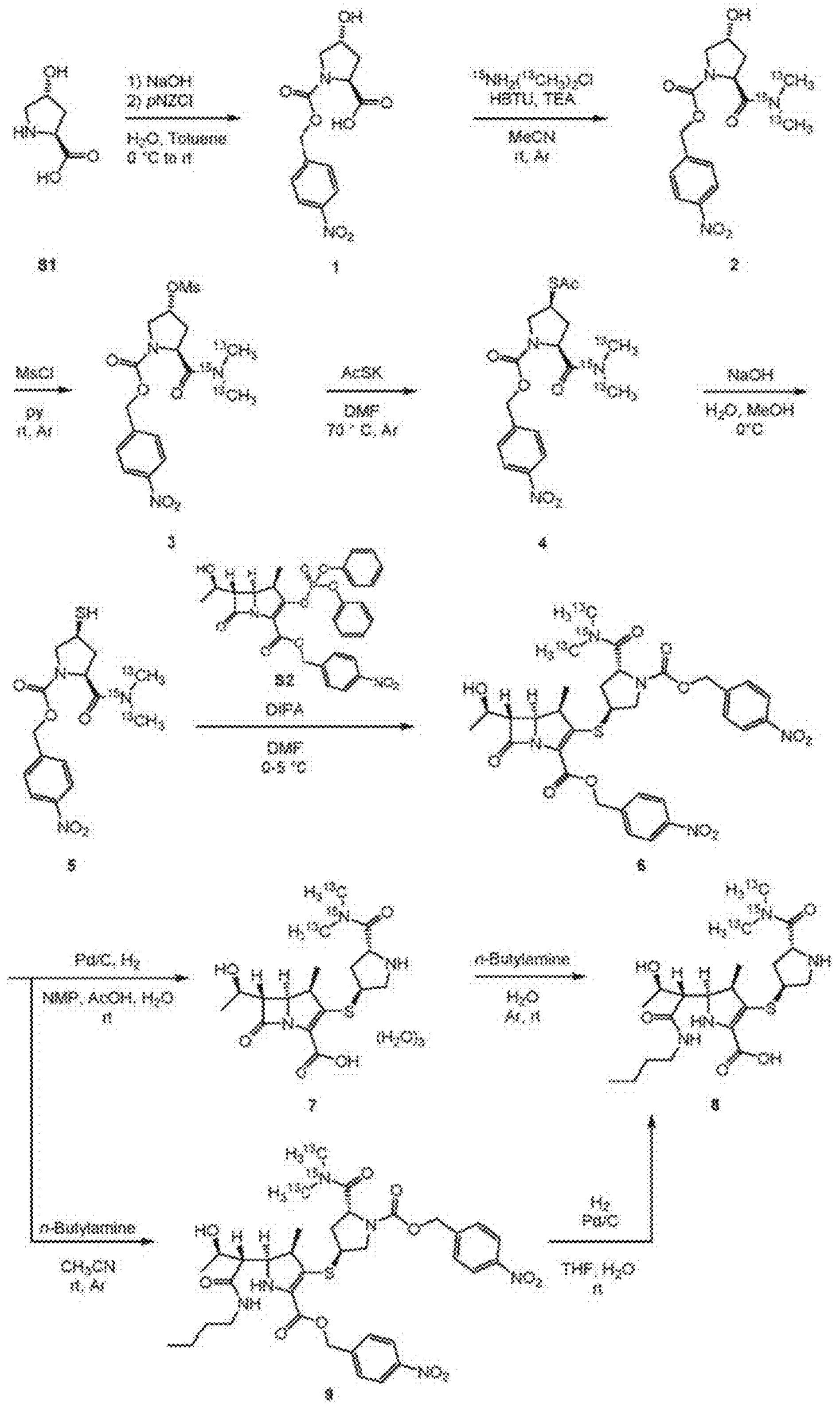

FIG. 7: Synthesis route for Meropenem-$^{13}C_2$-$^{15}N$ (7) and Meropenem-n-butylamide-$^{13}C_2$-$^{15}N$ (8).

Figure 8:
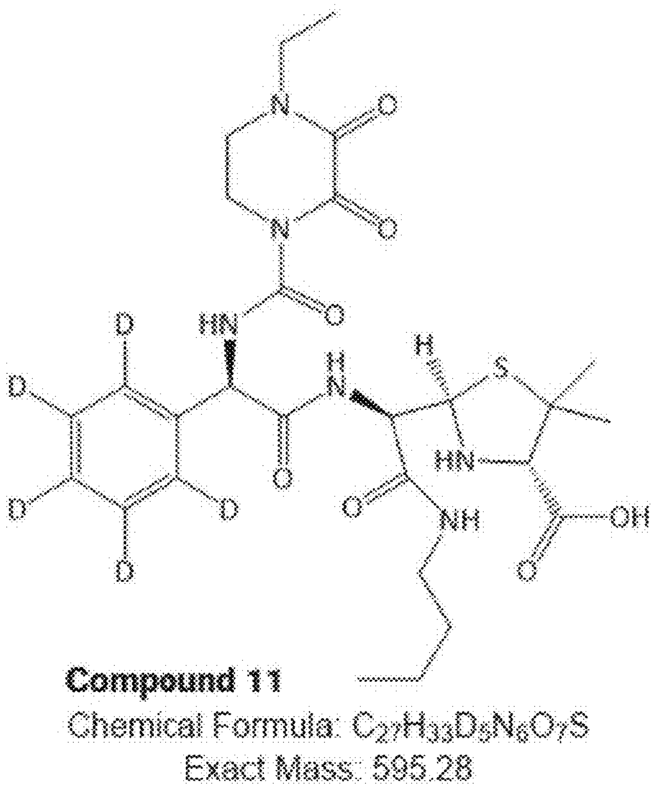

FIG. 8: Schematic drawing of deuterated Piperacillin ISTD (compound 11)

Figure 4:
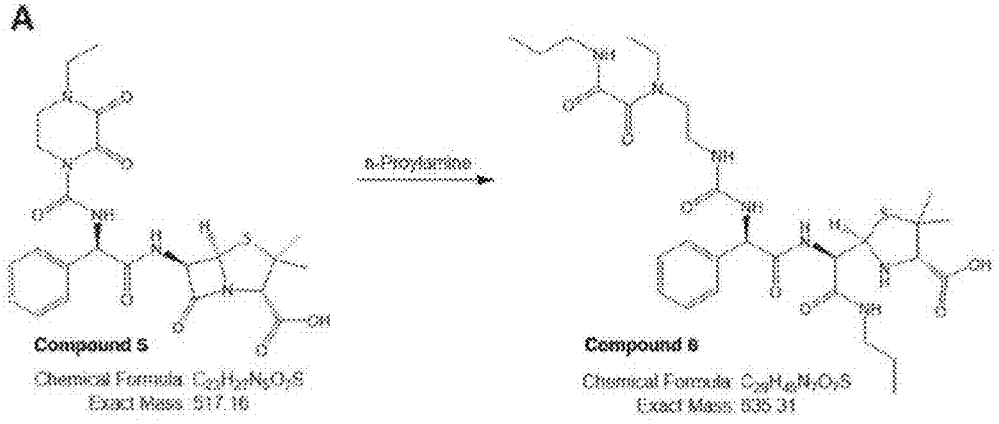
Figure 4:
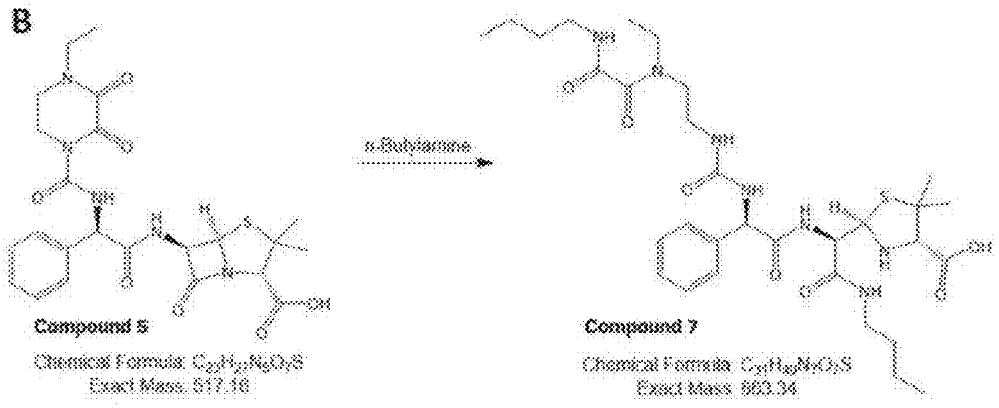
Figure 4:
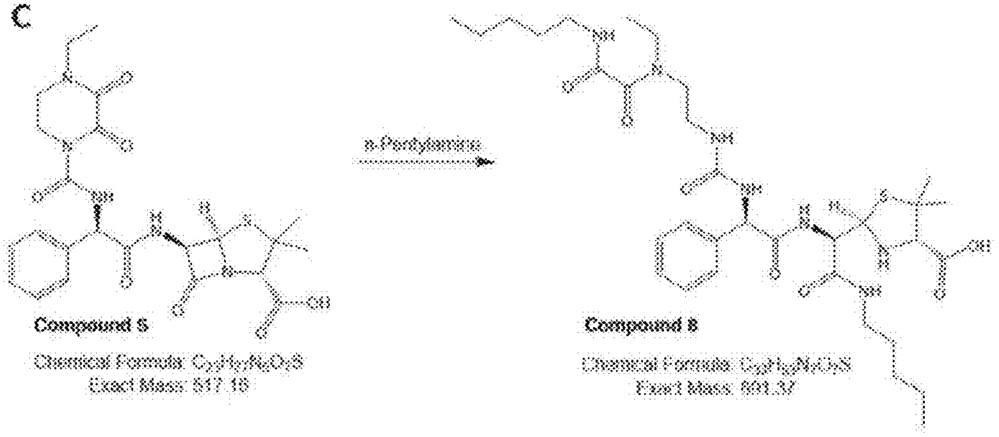
Figure 9:
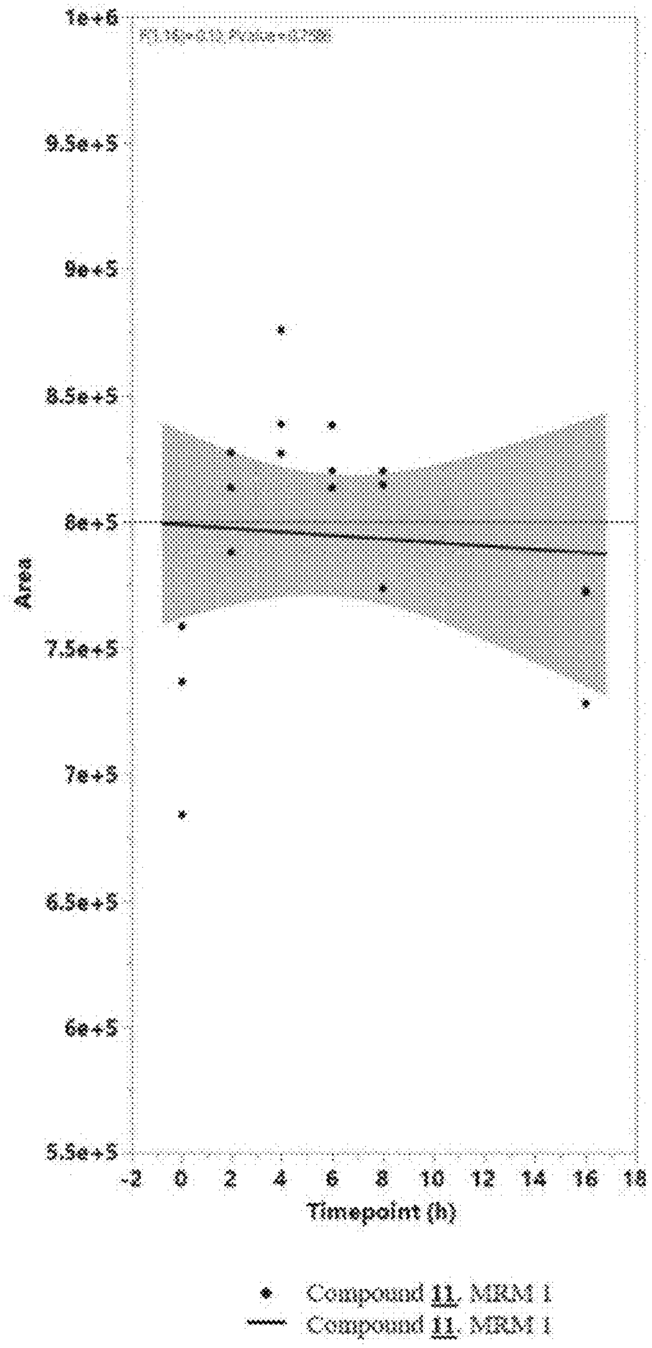
Figure 10:
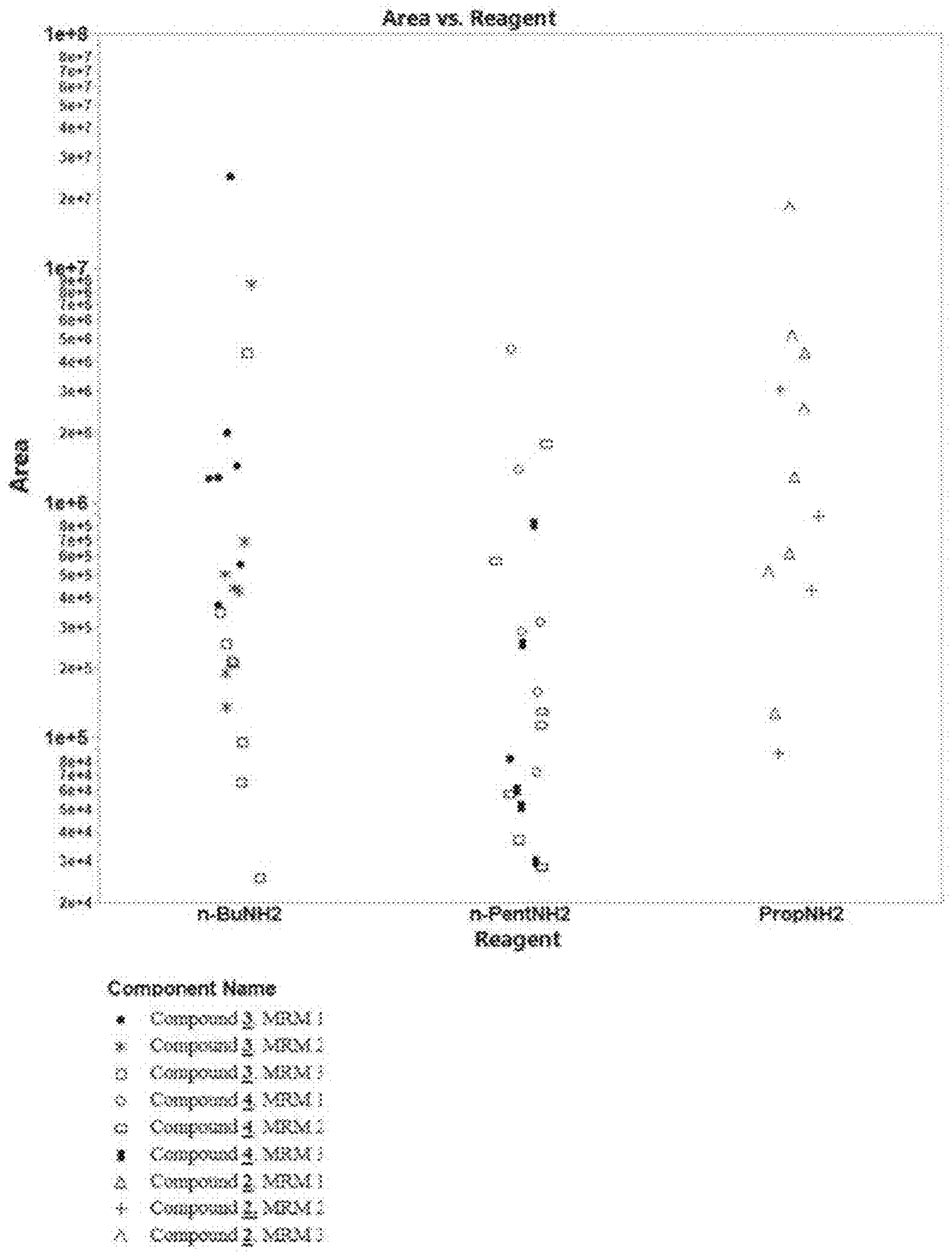
Figure 11:
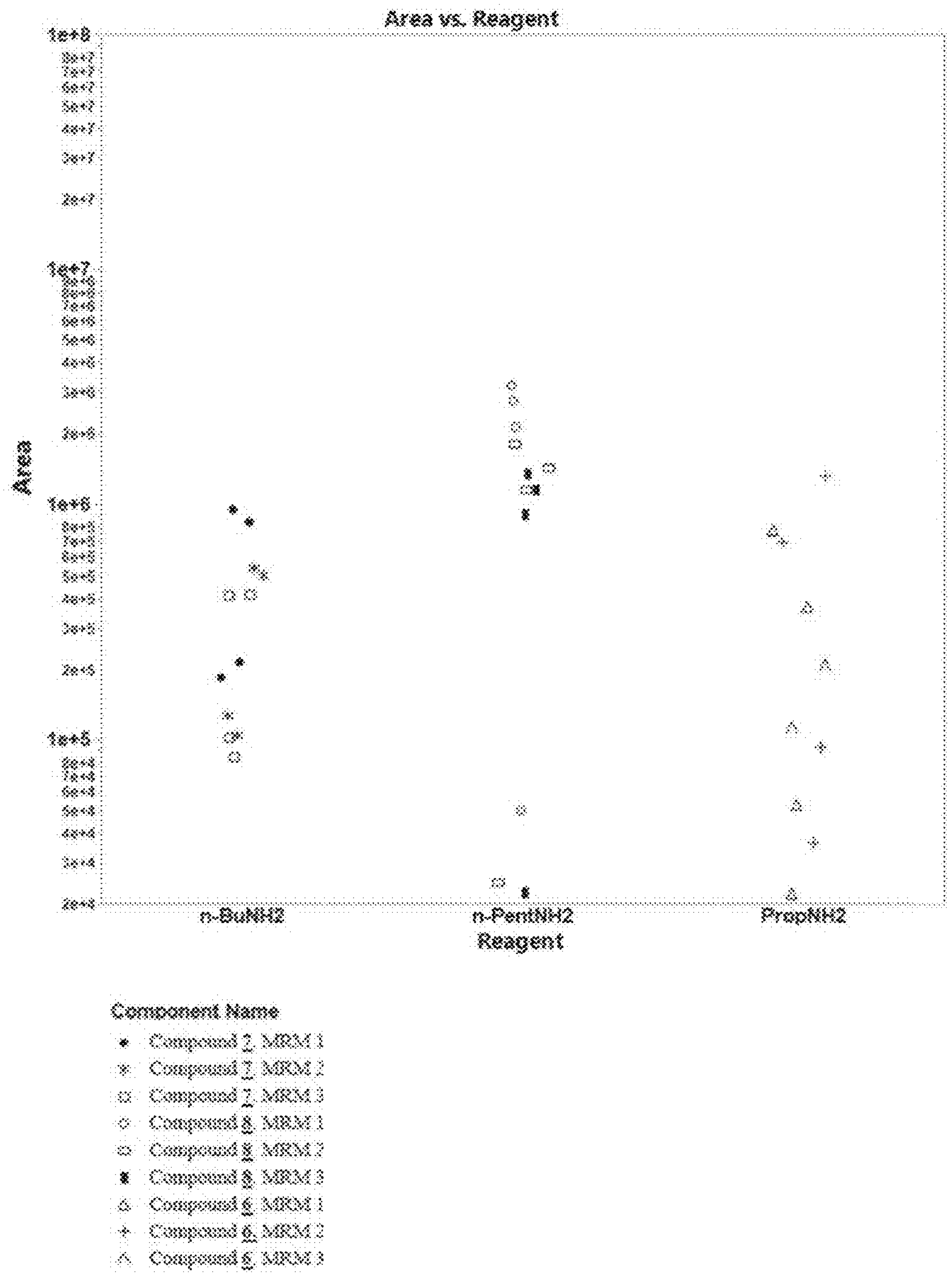

FIG. 9: Measured peak area over 16 h of single derivatized Piperacillin-D5 (compound 11, FIG. 8) in water at rt. For clarity, a reference line has been drawn through the average area values. Depicted with confidence fit and F-test FIG. 10: Measured Peak Areas of Meropenem (compound 2, 3 or 4, e.g. as shown in FIG. 3) derivatized with reagents propylamine, butylamine, and pentylamine at different reaction conditions FIG. 11: Measured Peak Areas of Piperazilin (compound 6, 7 or 8, e.g. as shown in FIG. 4) derivatized with reagents propylamine, butylamine, and pentylamine at different reaction conditions

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "measurement", "measuring" or "determining" preferably comprises a qualitative, a semi-quantitative or a quantitative measurement.

The term "automated" refers to methods or processes which are operated largely by automatic equipment, i.e. which are operate by machines or computers, in order to reduce the amount of work done by humans and the time taken to do the work. Thus, in an automated method, tasks that were previously performed by humans, are now performed by machines or computers. Typically, the users only need to configure the tool and define the process. The skilled person is well aware that at some minor points manual intervention may still be required, however the large extend of the method is performed automatically.

The term "Mass Spectrometry" ("Mass Spec" or "MS") relates to an analytical technology used to identify compounds by their mass. MS is a methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net electrical charge equal to one or more electron units. Negative ions are those having a net negative charge of one or more electron units, while positive ions are those having a net positive charge of one or more electron units. The MS method may be performed either in "negative ion mode", wherein negative ions are generated and detected, or in "positive ion mode" wherein positive ions are generated and detected.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Most sample workflows in MS further include sample preparation and/or enrichment steps, wherein e.g. the analyte(s) of interest are separated from the matrix using e.g. gas or liquid chromatography. Typically, for the mass spectrometry measurement, the following three steps are performed:

1. a sample comprising an analyte of interest is ionized, usually by adduct formation with cations, often by protonation to cations. Ionization source include but are not limited to electrospray ionization (ESI) and atmospheric pressure chemical ionization (APCI).
2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated Ni gas may be used to improve removal of solvent. The gas-phase ionization in APCI can be more effective than ESI for analyzing less-polar entity. 5"Multiple reaction mode" or "MRM" is a detection mode for a MS instrument in which a precursor ion and one or more fragment ions arc selectively detected.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the term "analyte", "analyte molecule", or "analyte(s) of interest" are used interchangeably referring the chemical species to be analysed. Chemical species suitable to be analysed, i.e. analytes, can be any kind of molecule present in a living organism, include but are not limited to nucleic acid, amino acids, peptides, proteins, fatty acids, lipids, carbohydrates, steroids, ketosteroids, secosteroids molecules. Analytes may also be any substance that has been internalized by the organism, such as but not limited to therapeutic drugs, drugs of abuse, toxin, or a metabolite of such a substance. Therapeutic drugs include antibiotics, i.e. "antibiotic analytes". Antibiotics are substance active against bacteria. Antibiotics are commonly classified based on their mechanism of action, chemical structure, or spectrum of activity. One class of antibiotics are β-lactam antibiotics. β-lactam antibiotics (beta-lactam antibiotics) are all antibiotic agents that contain a beta-lactam ring in their molecular structures. These include but are not limited to penicillin derivatives (penams), cephalosporins (cephems), monobactams, carbapenems and carbacephems. Most β-lactam antibiotics work by inhibiting cell wall biosynthesis in the bacterial organism and are the most widely used group of antibiotics. The effectiveness of these antibiotics relies on their ability to reach the PBP intact and their ability to bind to the penicillin binding proteins (PBP).

Analytes may be present in a sample of interest, e.g. a biological or clinical sample. The term "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, spinal fluid, urine, saliva, and lymphatic fluid, or solid samples such as dried blood spots and tissue extracts. Further examples of samples are cell cultures or tissue cultures.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), addition of hemolyzing reagent (HR) to whole blood samples, and the addition of enzymatic reagents to urine samples. Also the addition of internal standards (ISTD) is considered as pre-treatment of the sample.

Typically, an internal standard (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. $^{2}H$, $^{13}C$, or $^{15}N$ etc. label) of the analyte of interest.

The term "calibrator" refers to a complex or composition used as a standard or control, typically to construct a calibration curve allowing to determine the unknown concentration or amount of an analyte of interest in a given sample. The calibrators are run in a series over a predefined linear dynamic range of concentrations. The response from the testing of the calibrators is plotted on a signal versus concentration y-x axis graph. Typically, the chemical structure of a calibrators is identical or very similar (exhibiting very similar properties) to the chemical structure of the analyte of interest. The term "chromatography" refers to a process in which a chemical mixture carried by a liquid or gas is separated into components as a result of differential distribution of the chemical entities as they flow around or over a stationary liquid or solid phase.

The term "liquid chromatographie" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a narrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC modi include Hydrophilic interaction chromatography (HILIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

In the context of the present invention, the term "complex" refers to a chemical substance having a specific chemical structure. Said complex may comprise one or more functional units. Each unit may fulfil a different functionality, or two or more functional units may fulfil the same function.

In the context of the present invention, the term "nucleophile" refers to a chemical species that donates an electron pair to form a chemical bond. Nucleophiles that exists in a water medium include but are not limited to $-NH_2$, $-OH$, $-SH$, $-Se$, (R',R",R"')P, $N_3^-$, RCOOH, $F^-$, $Cl^-$, $Br^-$, $I^-$. In the context of the present invention, the term "nucleophilic derivatization reagent" or "nucleophilic derivatization reagent refers to reagents comprising such nucleophile. A nucleophilic derivatization reagent is able to react with a substance of interest, such as an analyte of interest, thereby forming a new complex comprising a nucleophilic unit and an analyte unit. The term "nucleophile" and "nucleophilic" can be used here and in the following interchangeable.

A "kit" is any manufacture (e.g. a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalized to receive in close confinement one or more container means such as vials, tubes, and the like. In particular, each of the container means or comprises one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments, etc.

Embodiments

Commonly used approaches to measure antibiotics, in particular β-lactam antibiotics, aim to defuse their instability. In contrast, the present invention does not defuse but employs the reactivity of the antibiotics by reacting them with a suitable nucleophile and thereby providing stable ISTDs and calibrators ensuring accurate measurements of antibiotics in patient samples.

Accordingly, in a first aspect, the present invention relates to a complex formed of an antibiotic substance and a nucleophilic derivatization reagent. The complex is obtained by reacting the antibiotic substance with the derivatization reagent resulting in the formation of an amide. In embodiments, wherein the antibiotic is a β-lactam containing antibiotic, the beta-lactam moiety is disrupted when the amide is formed. The resulting complex comprises an antibiotic unit and an nucleophile derivatization unit.

In embodiments, the nucleophilic derivatization reagent is a reagent comprising an amine group, in particular a primary or secondary amine. In particular embodiments, the nucleophilic derivatization reagent is a primary amine group. A primary amine group has the advantage that the incubation time can be reduced in comparison to a secondary amine.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms. Thus, MS interferences can be reduced or avoided.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is an antibiotic substance comprising a β-lactam moiety, i.e. in embodiments the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the complex comprises one or more isotopic label. In particular embodiments, the one or more isotopic label may be comprised in the nucleophile derivatization unit and/or the antibiotic unit of the complex. In particular embodiments, the one or more isotopic label is comprised in the antibiotic unit of the complex. In particular embodiments, the one or more isotopic labels is deuterium, $^{13}C$, $^{15}N$, and/or $^{18}O$.

In particular embodiments, all isotopic labels are identical label. In alternative embodiments, the isotopic label may be different, i.e. may comprise two, three or four different isotopic labels.

In particular embodiments, the antibiotic unit of the complex comprises 1 to 10 isotopic labels, in particular which are all identical. In particular embodiments, the antibiotic unit of the complex comprises 1 to 8 isotopic labels, in particular 1 to 5 isotopic labels. In particular embodiments the antibiotic unit of the complex comprises 1, 2, 3, 4, or 5 isotopic labels. In particular embodiments, the antibiotic unit of the complex comprises 5 deuterium labels.

In a second aspect, the present invention relates to a composition comprising the complex formed of an antibiotic substance and a nucleophilic derivatization reagent. In embodiments, the composition further comprises a solvent, in particular a solvent selected from the group consisting of water, $CH_3CN$, THF, Dioxanes, DMF, DMSO, acetone, t-butyl alcohol, diglyme, DME, MeOH, EtOH, 1-PrOH, 2-PrOH, ethylene glycol, Hexamethylphosphoramiede (HMPA), Hexamethylphosphorous triamide (HMPT), and glycerin. In particular embodiments, the solvent selected from the group consisting of water, $CH_3CN$, THF, Dioxanes, DMF, DMSO, acetone, t-butyl alcohol, diglyme, and DME.

In embodiments, the composition further comprises a non-nucleophilic base that is stable and miscible with water.

In particular embodiments, the non-nucleophilic base is selected from the group consisting of DBU, $Na_3PO_4$, $Na_2CO_3$, and $Cs_2CO_3$.

The complex is obtained by reacting the antibiotic substance with the derivatization reagent resulting in the formation of an amide. In embodiments, wherein the antibiotic is a β-lactam containing antibiotic, the β-lactam moiety is disrupted when the amide is formed. The resulting complex comprises an antibiotic unit and a nucleophile derivatization unit.

In embodiments, the nucleophilic derivatization reagent is a reagent comprising an amine group, in particular a primary or secondary amine. In particular embodiments, the nucleophilic derivatization reagent is a primary amine group.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is an antibiotic substance comprising a β-lactam moiety, i.e. in embodiments the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the complex comprises one or more isotopic labels. In particular embodiments, the one or more isotopic labels may be comprised in the nucleophile derivatization unit and/or the antibiotic unit of the complex. In particular embodiments, the one or more isotopic label is comprised in the antibiotic unit of the complex. In particular embodiments, the one or more isotopic label is deuterium, $^{13}C$, $^{15}N$, and/or $^{18}O$.

In particular embodiments, all isotopic labels are identical labels. In alternative embodiments, the isotopic label may be different, i.e. may comprise two, three or four different isotopic labels.

In particular embodiments, the antibiotic unit of the complex comprises 1 to 10 isotopic labels, in particular which are all identical. In particular embodiments, the antibiotic unit of the complex comprises 1 to 8 isotopic label, in particular 1 to 5 isotopic label. In particular embodiments the antibiotic unit of the complex comprises 1, 2, 3, 4, or 5 isotopic labels. In particular embodiments, the antibiotic unit of the complex comprises 5 deuterium labels.

In a third aspect, the present invention relates to a kit comprising a) the complex of the first aspect, or the composition of the second aspect, and b) a package insert.

In a fourth aspect, the present invention relates to the use of a complex of the first aspect, or the composition of the second aspect, or the kit of the third aspect, for Mass Spec measurements.

In particular embodiments, the complex or the composition or the kit is used to determine the amount or concentration of an antibiotic analyte in a patients sample via Mass Spec.

In particular embodiments, the complex or the composition is used to serve as internal standard (ISTD) in the measurement of the amount or concentration of an antibiotic analyte in a patients sample via Mass Spec. In particular embodiments, the complex of the first aspect or the composition of the second aspect is used as ISTD by adding a pre-defined amount or concentration to a sample of interest. In particular, the complex of the first aspect or the composition of the second aspect adding to a sample prior to the measurement of the sample.

In particular embodiments, the complex or the composition is used to serve as calibrator for the measurement of the amount or concentration of an antibiotic analyte in a patient sample via Mass Spec. In particular embodiments, the complex of the first aspect or the composition of the second aspect is used.

In a fifth aspect, the present invention relates to the use of a nucleophilic derivatization reagent to stabilize an antibiotic substance. In particular, the nucleophilic derivatization reagent is used to derivatize and thereby stabilize an antibiotic substance to be suitable as ISTD and/or calibrator in Mass Spec Measurements. In embodiments, the nucleophilic derivatization reagent prevents the hydrolyzation of the antibiotic substance. The nucleophilic derivatization reagent prevents the hydrolyzation by reacting with the antibiotic substance to form a complex. In embodiments, wherein the antibiotic is a β-lactam containing antibiotic, the β-lactam moiety is disrupted when the complex is formed. The resulting complex comprises an antibiotic unit and a nucleophile derivatization unit.

In embodiments, the nucleophilic derivatization reagent stabilized the antibiotic substance for more than for more than 12 hours, for more than 24 hours, for more than 48 hours, for more than 7 days, for more than 2 weeks, for more than 4 weeks, for more than 2 months, for more than 3 months, for more than 4 months, for more than 5 months, or for more than 6 months. In particular embodiments, the nucleophilic derivatization reagent stabilized the antibiotic substance for more than 12 hours. In particular embodiments, the nucleophilic derivatization reagent stabilized the antibiotic substance for more than 24 hours, in particular for more than 48 hours. In particular embodiments, the nucleophilic derivatization reagent stabilized the antibiotic substance for more than 2 weeks. In particular embodiments, the nucleophilic derivatization reagent stabilized the antibiotic substance for more than 2 months. In particular embodiments, the nucleophilic derivatization reagent stabilized the antibiotic substance for at least 16 hours. In particular embodiments, the nucleophilic derivatization reagent stabilized the antibiotic substance for 16 hours.

In embodiments, the nucleophilic derivatization reagents is used to stabilize the antibiotic substance which allows for the use of the derivatized antibiotic substance as internal standard (ISTD) Mass Spec measurements.

In embodiments, the nucleophilic derivatization reagent is a reagent comprising an amine group, in particular a primary or secondary amine. In particular embodiments, the nucleophilic derivatization reagent is a primary amine group.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is a antibiotic substance comprising a β-lactam moiety, i.e. the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the antibiotic substance and/or the nucleophilic derivatization reagent comprises one or more isotopic labels. In particular embodiments, the one or more isotopic labels may be comprised in the nucleophile derivatization unit and/or the antibiotic unit of the complex. In particular embodiments, the one or more isotopic label is comprises in the antibiotic unit of the complex. In particular embodiments, the one or more isotopic label is deuterium, $^{13}C$, $^{15}N$, and/or $^{18}O$. In particular embodiments, all isotopic labels are identical labels. In alternative embodiments, the isotopic label may be different, i.e. may comprise two, three or four different isotopic labels.

In particular embodiments, the antibiotic unit of the complex comprises 1 to 10 isotopic label. In particular embodiments, the antibiotic unit of the complex comprises 1 to 8 isotopic labels, in particular 1 to 5 isotopic labels. In particular embodiments the antibiotic unit of the complex comprises 1, 2, 3, 4, or 5 isotopic label.

In particular embodiments, the antibiotic unit of the complex comprises 5 deuterium label.

In a sixth aspect, the present invention relates to a derivatized antibiotic substance, in particular a derivatized antibiotic substance which is suitable to be used as ISTD and/or calibrator in Mass Spec measurements.

In embodiments, the antibiotic substance is derivatized by a nucleophilic derivatization reagent. In embodiments, the nucleophilic derivatization reagent prevents the hydrolyzation by reacting with the antibiotic substance to form a complex. In embodiments, wherein the antibiotic is a β-lactam containing antibiotic, the β-lactam moiety is disrupted when the complex is formed. The resulting complex comprises an antibiotic unit and an nucleophile derivatization unit.

In embodiments, the nucleophilic derivatization reagent stabilized the antibiotic substance for more than for more than 12 hours, for more than 24 hours, for more than 48 hours, for more than 7 days, for more than 2 weeks, for more than 4 weeks, for more than 2 months, for more than 3 months, for more than 4 months, for more than 5 months, or for more than 6 months. In particular embodiments, the nucleophilic derivatization reagent stabilized the antibiotic substance for more than 12 hours. In particular embodiments, the nucleophilic derivatization reagent stabilized the antibiotic substance for more than 24 hours, in particular for more than 48 hours. In particular embodiments, the nucleophilic derivatization reagent stabilized the antibiotic substance for more than 2 weeks. In particular embodiments, the nucleophilic derivatization reagent stabilized the antibiotic substance for more than 2 months. In particular embodiments, the nucleophilic derivatization reagent stabilized the antibiotic substance for at least 16 hours. In particular embodiments, the nucleophilic derivatization reagent stabilized the antibiotic substance for 16 hours.

In embodiments, the nucleophilic derivatization reagent is a reagent comprising an amine group, in particular a primary or secondary amine. In particular embodiments, the nucleophilic derivatization reagent is a primary amine group.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is a antibiotic substance comprising a β-lactam moiety, i.e. the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the antibiotic substance and/or the nucleophilic derivatization reagent comprises one or more isotopic label. In particular embodiments, the one or more isotopic label may be comprised in the nucleophile derivatization unit and/or the antibiotic unit of the derivatized antibiotic substance. In particular embodiments, the one or more isotopic label is comprises in the antibiotic unit of the derivatized antibiotic substance. In particular embodiments, the one or more isotopic label is deuterium, $^{13}C$, $^{15}N$, and/or $^{18}O$. In particular embodiments, all isotopic label are identical labels. In alternative embodiments, the isotopic label may be different, i.e. may comprise two, three or four different isotopic labels.

In particular embodiments, the antibiotic unit of the derivatized antibiotic substance comprises 1 to 10 isotopic labels. In particular embodiments, the antibiotic unit of the derivatized antibiotic substance comprises 1 to 8 isotopic labels, in particular 1 to 5 isotopic labels. In particular embodiments the antibiotic unit of the derivatized antibiotic substance comprises 1, 2, 3, 4, or 5 isotopic labels.

In particular embodiments, the antibiotic unit of the derivatized antibiotic substance comprises 5 deuterium labels.

In particular embodiments, where it is intended to use the derivatized antibiotic substance as calibrator, the derivatized antibiotic substance does not comprise an isotopic label.

In particular embodiments, where it is intended to use the derivatized antibiotic substance as ISTD, the derivatized antibiotic substance comprises at least one isotopic label.

In a seventh aspect, the present invention relates to the use of a derivatized antibiotic as ISTD and/or calibrator in Mass Spec Measurements.

In embodiments, the antibiotic substance is derivatized by a nucleophilic derivatization reagent. In embodiments, the nucleophilic derivatization reagents stabilizes the antibiotic substance. In embodiments, the nucleophilic derivatization reagent prevents the hydrolyzation by reacting with the antibiotic substance to form a complex. In embodiments, wherein the antibiotic is a β-lactam containing antibiotic, the β-lactam moiety is disrupted when the complex is formed. The resulting complex comprises an antibiotic unit and a nucleophile derivatization unit.

In embodiments, the nucleophilic derivatization reagent stabilized the antibiotic substance for more than for more than 12 hours, for more than 24 hours, for more than 48 hours, for more than 7 days, for more than 2 weeks, for more than 4 weeks, for more than 2 months, for more than 3 months, for more than 4 months, for more than 5 months, or for more than 6 months. In particular embodiments, the nucleophilic derivatization reagent stabilized the antibiotic substance for more than 12 hours. In particular embodiments, the nucleophilic derivatization reagent stabilized the antibiotic substance for more than 24 hours, in particular for more than 48 hours. In particular embodiments, the nucleophilic derivatization reagent stabilized the antibiotic substance for more than 2 weeks. In particular embodiments, the nucleophilic derivatization reagent stabilized the antibiotic substance for more than 2 months. In particular embodiments, the nucleophilic derivatization reagent stabilized the antibiotic substance for at least 16 hours. In particular embodiments, the nucleophilic derivatization reagent stabilized the antibiotic substance for 16 hours.

In embodiments, the nucleophilic derivatization reagent is an reagent comprising an amine group, in particular a primary or secondary amine. In particular embodiments, the nucleophilic derivatization reagent is a primary amine group.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is a antibiotic substance comprising a β-lactam moiety, i.e. the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the antibiotic substance and/or the nucleophilic derivatization reagent comprises one or more isotopic label. In particular embodiments, the one or more isotopic label may be comprised in the nucleophile derivatization unit and/or the antibiotic unit of the complex. In particular embodiments, the one or more isotopic label is comprises in the antibiotic unit of the complex. In particular embodiments, the one or more isotopic label is deuterium, $^{11}C$, $^{15}N$, and/or $^{18}O$. In particular embodiments, all isotopic label are identical label. In alternative embodiments, the isotopic label may be different, i.e. may comprise two, three or four different isotopic labels.

In particular embodiments, the antibiotic unit of the complex comprises 1 to 10 isotopic labels. In particular embodiments, the antibiotic unit of the complex comprises 1 to 8 isotopic labels, in particular 1 to 5 isotopic labels. In particular embodiments the antibiotic unit of the complex comprises 1, 2, 3, 4, or 5 isotopic labels.

In particular embodiments, the antibiotic unit of the complex comprises 5 deuterium labels.

In particular embodiments, the derivatized antibiotic substance is used as calibrator and does not comprise an isotopic label.

In particular embodiments, the derivatized antibiotic substance is used as ISTD and comprises at least one isotopic label.

In an eighth aspect, the present invention relates to method of producing a stabilized antibiotic substance, comprising derivatizing an antibiotic substance with a nucleophile derivatization reagent.

In embodiments, the nucleophilic derivatization reagent is provided in an excess of at least 2.5E8, in particular in an excess of between 1E5 and 1E10 compared to the amount of antibiotic substance present.

In embodiments, the nucleophilic derivatization reagent is a reagent comprising an amine group, in particular a primary or secondary amine. In particular embodiments, the nucleophilic derivatization reagent is a primary amine group.

In embodiments, the nucleophilic derivatization reagent comprises more than 3 C-atoms, in particular 3 to 20 C-atoms. In particular embodiments, the nucleophilic derivatization reagent comprises 3 to 10 C-atoms, in particular 3-5 C-atoms. In particular embodiments, the nucleophilic derivatization reagent comprises 4 C-atoms.

In embodiments, the nucleophilic derivatization reagent is linear or branched, in particular a linear amine, in particular a linear primary amine. In particular embodiments, the nucleophilic derivatization reagent is a linear primary amine comprising 3 to 5 C-atoms.

In embodiments, the nucleophilic derivatization reagent is selected from the group consisting of propylamine, butylamine, and pentylamine. In particular embodiments, the nucleophilic derivatization reagent is a primary linear butylamine.

In embodiments, the antibiotic substance is a antibiotic substance comprising a β-lactam moiety, i.e. the antibiotic substance is a β-lactam antibiotic.

In embodiments, the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

In particular embodiments, the antibiotic substance is Meropenem or Piperacillin.

In embodiments, the antibiotic substance and/or the nucleophilic derivatization reagent comprises one or more isotopic label. In particular embodiments, the one or more isotopic label may be comprised in the nucleophile derivatization unit and/or the antibiotic unit of the complex. In particular embodiments, the one or more isotopic label is comprises in the antibiotic unit of the complex. In particular embodiments, the one or more isotopic label is deuterium, $^{13}C$, $^{15}N$, and/or $^{18}O$. In particular embodiments, all isotopic labels are identical labels. In alternative embodiments, the isotopic label may be different, i.e. may comprise two, three or four different isotopic labels.

In particular embodiments, the antibiotic unit of the complex comprises 1 to 10 isotopic labels. In particular embodiments, the antibiotic unit of the complex comprises 1 to 8 isotopic labels, in particular 1 to 5 isotopic labels. In particular embodiments the antibiotic unit of the complex comprises 1, 2, 3, 4, or 5 isotopic labels.

In particular embodiments, the antibiotic unit of the complex comprises 5 deuterium labels.

The present invention further relates to the following items:

1) A complex formed of an antibiotic substance and a nucleophilic derivatization reagent.
2) The complex of item 1, wherein the nucleophilic derivatization reagent is a reagent comprising an amine group, in particular a primary or secondary amine, in particular a primary amine group.

3) The complex of item 1 or 2, wherein the nucleophilic derivatization reagent comprises more than 3 C-atoms, in particular 3 to 20 C-atoms, in particular 3 to 10 C-atoms, in particular 3-5 C-atoms, in particular 4 C-atoms.

4) The complex of any of items 1 to 3, wherein the nucleophilic derivatization reagent is linear or branched, in particular a linear amine, in particular a linear primary amine, in particular a linear primary amine comprising 3 to 5 C-atoms.

5) The complex of any of items 1 to 4, wherein the derivatization reagent is selected from the group consisting of propylamine, butylamine, or pentylamine, in particular primary linear butylamine.

6) The complex of any of items 1 to 5, wherein the antibiotic substance is a β-lactam antibiotic substance.

7) The complex of any of items 1 to 6, wherein the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, imipenem, Doripenem, Ertapenem, Meropenem, Aztreonam, and Mecillinam.

8) The complex of any of items 1 to 6, wherein the antibiotic substance is Meropenem or Piperacillin.

9) The complex of any of items 1 to 8 comprising an isotopic labels.

10) A composition comprising the complex of any of items 1 to 9.

11) Composition comprising the complex of any of items 1 to 9, wherein the composition further comprises a solvent, in particular a solvent selected from the group consisting of water, $CH_3CN$, THF, Dioxanes, DMF, DMSO, acetone, t-butyl alcohol, diglyme, DME, MeOH, EtOH, 1-PrOH, 2-PrOH, ethylene glycol, Hexamethylphosphoramiede (HMPA), Hexamethylphosphorous triamide (HMPT), and glycerin.

12) The composition of item 11, wherein the solvent selected from the group consisting of water, $CH_3CN$, THF, Dioxanes, DMF, DMSO, acetone, t-butyl alcohol, diglyme, and DME. 13) The composition of any of items 11 to 12, further comprising a non-nucleophilic base that is stable and miscible with water, in particular selected from the group consisting of DBU, $Na_3PO_4$, $Na_2CO_3$, and $Cs_2CO_3$.

14) A kit comprising a) the complex of any of items 1 to 9 or the composition of any of items 10 to 13, and b) a package insert.

15) Use of a complex of any of items 1 to 9, or the composition of any of items 10 to 13, or the kit of item 14, for Mass Spec measurements.

16) Use of a complex of any of items 1 to 9, or the composition of any of items 10 to 13, or the kit of item 14, as an internal standard and/or calibrator for Mass Spec measurements.

17) Use of a nucleophilic derivatization reagent to stabilize an antibiotic substance, in particular to be suitable as ISTD and/or calibrator in Mass Spec Measurements.

18) The use of item 17, wherein the nucleophilic derivatization reagent is a reagent comprising an amine group, in particular a primary or secondary amine, in particular a primary amine group.

19) The use of item 17 or 18, wherein the nucleophilic derivatization reagent comprises more than 3 C-atoms, in particular 3 to 20 C-atoms, in particular 3 to 10 C-atoms, in particular 3-5 C-atoms, in particular 4 C-atoms.

20) The use of any of items 17 to 19, wherein the nucleophilic derivatization reagent is linear or branched, in particular a linear amine, in particular a linear primary amine, in particular a linear primary amine comprising 3 to 5 C-atoms.

21) The use of any of items 17 to 20, wherein the derivatization reagent is selected from the group consisting of propylamine, butylamine, or pentylamine, in particular primary linear butylamine.

22) The use of any of items 17 to 21, wherein the antibiotic substance is a β-lactam antibiotic substance.

23) The use of any of items 17 to 22, wherein the antibiotic substance is selected from the group consisting of Amoxicillin, Ampicillin, Bacampicillin, Carbenicillin, Cloxacillin, Dicloxacillin, Flucloxacillin, Mezlocillin, Nafcillin, Oxacillin, Temocillin, Pheneticillin, Penicillin G, Penicillin V, Piperacillin, Azlocillin, Pivampicillin, Pivmecillinam, Ticarcillin, Cefacetrile (cephacetrile), Cefadroxil (cefadroxyl), Cefalexin (cephalexin), Cefalexin (cephalexin), Cefaloglycin (cephaloglycin), Cefalonium (cephalonium), Cefaloridine (cephaloradine), Cefalotin (cephalothin), Cefalotin (cephalothin), Cefapirin (cephapirin), Cefatrizine, Cefazaflur, Cefazedone, Cefazolin (cephazolin), Cefradine (cephradine), Cefradine (cephradine), Cefroxadine, Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Ceftolozane, Imipenem, Doripenem, Ertapenem, Meropenem, Aztreonam, and Mecillinam.

24) The use of any of items 17 to 23, wherein the antibiotic substance is Meropenem or Piperacillin.

25) The use of any of items 17 to 24, wherein the nucleophilic derivatization reagent prevents the hydrolyzation of the antibiotic substance.

26) The use of any of items 17 to 25, wherein the nucleophilic derivatization reagent stabilized the antibiotic substance for more than 12 hours.

27) A derivatized antibiotic substance suitable as ISTD in Mass Spec Measurements.

28) Use of a derivatized antibiotic as ISTD and/or calibrator in Mass Spec Measurements.

29) A method of producing a stabilized antibiotic substance, comprising derivatizing an antibiotic substance with a nucleophilic derivatization reagent.

30) A method of item 29, wherein the nucleophilic derivatization reagent is provided in an excess of at least 2.5E8, in particular in an excess of between 1E5 and 1E10 compared to the amount of antibiotic substance present.

Examples

The following examples are provided to illustrate, but not to limit the presently claimed invention.

General methods: All reactions were magnetically stirred and carried out under a positive pressure of inert gas ($N_2$ or argon) utilizing standard Schlenk-techniques. Glassware was dried repeatedly at 620° C. in vacuo prior to use. Liquid reagents and solvents were added by syringes or oven-dried stainless steel cannulas through rubber septa. Solids were added under inert gas counter flow or were dissolved in appropriate solvents. Low-temperature reactions were carried out in a Dewar vessel filled with a cooling agent: acetone/dry ice (−78° C.) or $H_2O$/ice (0° C.). Reaction temperatures above room temperature were conducted in a heated oil bath. If literature-known procedures were followed, the respective reference was added to the experimental details. Yields refer to isolated homogenous and spectroscopically pure materials, if not indicated otherwise.

Solvents and Reagents: Dry solvents, such as dichloromethane ($CH_2Cl_2$), tetrahydrofuran (THF), pyridine, N,N-dimethylformamide (DMF), and acetonitrile (MeCN) were purchased from commercial suppliers and used as received. Solvents for extraction and flash column chromatography were purchased in HPLC grade. D-(−)-α-Phenylglycine-$D_5$ (1, FIG. 6) was purchased from *Toronto Research Chemicals*. Compound S2 (FIG. 7) was purchased from Ambeed Inc. Compound 2 (FIG. 6) was synthesized from (+)-6-aminopenicillanic acid (S1, FIG. 6) according to De Rosa, et al. (*Molecules* 2015, 20, 22044-22057). All other reagents and solvents were purchased from chemical suppliers (Sigma-Aldrich, Acros Organics, Alfa Aesar, TCI Europe, abcr) and were used as received.

NMR Spectroscopy: NMR spectra were measured on an Agilent 400-MR DD2 400 MHz spectrometer equipped with a OneNMR Probe operating at 400 MHz for proton nuclei (100 MHz for carbon nuclei). DMSO-$d_6$ and $CDCl_3$ were purchased from Sigma-Aldrich. The $^1H$ NMR shifts are reported in ppm related to the residual shift of TMS. $^1H$ NMR shifts were calibrated to residual solvent resonances: DMSO-$d_6$ (2.50 ppm) and $CDCl_3$ (7.26 ppm). $^{13}C$ NMR shifts were calibrated to the center of the multiplet signal of the residual solvent resonance: DMSO-$d_6$ (29.84 ppm) and $CDCl_3$ (77.16 ppm). $^1H$ NMR spectroscopic data are reported as follows: Chemical shift in ppm (multiplicity, coupling constants J, integration intensity). The multiplicities are abbreviated with s (singlet), br (broad signal), d (doublet), t (triplet), q (quartet), m (multiplet) and mc (centrosymmetric multiplet). In case of combined multiplicities, the multiplicity with the lesser coupling constant is stated first. Except for multiplets, the chemical shift of all signals, as well for centrosymmetric multiplets, is reported as the center of the resonance range. Coupling constants J are reported in Hz. All NMR spectra were analyzed using the program ACD/Spectrus Processor 2015.2.7 from Advanced Chemistry Development, Inc.

Mass Spectrometry: Low resolution mass spectra (LRMS) were recorded on a HPLC-MS system from the Waters GmbH (2695 Separations Module, 996 Photodiode Array Detector, MicromassZQ, Grace Vydac 218TP C18 5u) that was computer-controlled through Waters MassLynx V4.1. Only characteristic molecule fragments or molecule ion peaks are indicated for each analyte.

Example 1: Stability of Native Piperacillin (Compound 5, See FIG. 1)

The stability of native Piperacillin as well as its hydrolyzed forms was investigated (compounds 5, 9a, 9b and 10, respectively. From the hydrolysis pathway of Piperacillin (compound 5, see schematic drawing in FIG. 1) it is obvious that this compound hydrolyzed both on the piperazin ring and the lactam moiety, only one of both compounds is monitored to account for the loss or degradation of native Piperacillin (compound 5)). To this end, these compounds were freshly weighed and dissolved in water at a concentration of 1 mg/mL by rolling or stirring for 15 minutes at room temperature. Subsequently, these compounds were diluted to 5 μg/mL and measured with a suitable LC-MS/MS method at timepoints 0, 2, 4, 6, 8 and 16 h. For this, a Sunshell C18 (2.6 μm, 2.1 mm×50 mm) column with Solvent A: water with 0.1% HCOOH and Solvent B: $CH_3CN$ with 0.1% HCOOH and a flow of 0.6 mL per minute were used on an Agilent Infinity II multisampler/Pump system connected to an AB Sciex 6500+MS. The peaks were integrated using MultiQuant software and the areas of these peaks depicted in the graphs in FIGS. 2A and 2B.

FIGS. 2A and 2B show the obtained areas for one MRM transition for native Piperacillin (compound 5) and its hydrolyzed forms (compounds 9a/9b), respectively. It is clear that the obtained peak-areas vary significantly over time (F-test, yielding a P value of <0.0001) with the peak-areas of the native form decreasing and the peak-areas of the hydrolyzed forms (compounds 9a/9b) significantly increasing (F-test, yielding a P value of <0.0001). The reason for this is the hydrolyzation or hydrolysis reaction (as is schematically depicted in FIG. 1).

Example 2: The Synthesis of Piperacillin-$D_5$ Monohydrate (8) and its Mono n-Butylamine Addition Product (9) (Schematic Drawing and Compound Numbering See FIG. 6)

All reactions were magnetically stirred and carried out under a positive pressure of inert gas ($N_2$ or argon) utilizing standard Schlenk-techniques. Glassware was dried repeatedly at 620° C. in vacuo prior to use. Liquid reagents and solvents were added by syringes or oven-dried stainless steel cannulas through rubber septa. Solids were added under inert gas counter flow or were dissolved in appropriate solvents. Low-temperature reactions were carried out in a Dewar vessel filled with a cooling agent: acetone/dry ice (−78° C.) or $H_2O$/ice (0° C.). Reaction temperatures above room temperature were conducted in a heated oil bath. If literature-known procedures were followed, the respective reference was added to the experimental details. Yields refer to isolated homogenous and spectroscopically pure materials, if not indicated otherwise.

Solvents and Reagents: Dry solvents, such as dichloromethane ($CH_2Cl_2$), tetrahydrofuran (THF) and acetonitrile (MeCN) were purchased from commercial suppliers and used as received. Solvents for extraction and flash column chromatography were purchased in HPLC grade. D-(−)-α-Phenylglycine-$D_5$ (1) was purchased from Toronto Research Chemicals. Compound 2 was synthesized from (+)-6-aminopenicillanic acid (S1) according to De Rosa, et al. 2015 (Molecules 2015, 20, 22044-22057). All other reagents and solvents were purchased from chemical suppliers (Sigma-Aldrich, Acros Organics, Alfa Aesar, TCI Europe, abcr) and were used as received.

Synthetic Procedures

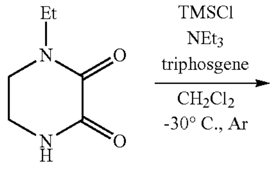

3
$C_6H_{10}N_2O_2$
$M_w$ = 142.16

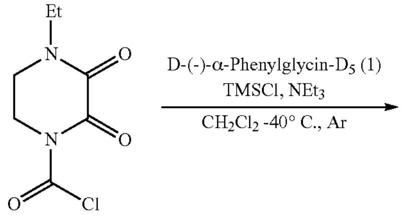

4
$C_7H_9ClN_2O_3$
$M_w$ = 204.61

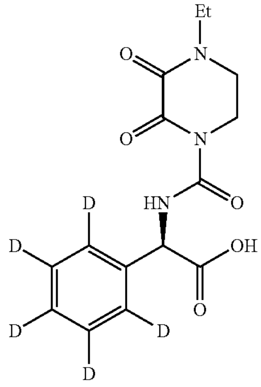

5
$C_{15}H_{12}D_5N_3O_5$
$M_w$ = 324.35

Acid (5): 1-Ethylpiperazine-2,3-dione (455 mg, 3.20 mmol, 1.00 eq.) was dissolved in dry dichloromethane (8.9 mL) under argon atmosphere at room temperature. After cooling to 0° C., dry triethylamine (616 μL, 4.42 mmol, 1.38 eq.) and then TMSCl (447 μL, 3.53 mmol, 1.10 eq.) were added and the resulting mixture stirred for one hour at room temperature. The reaction was then cooled to −30° C., triphosgene (361 mg, 1.21 mmol, 0.38 eq.) was added in one batch and stirring was continued for another hour. Thorough drying in vacuo yielded intermediate 4 as moisture sensitive foam, which was directly redissolved in dry dichloromethane (8.9 mL) for further synthesis. Meanwhile, D-(−)-α-Phenylglycine (1, 500 mg, 3.20 mmol. 1.00 eq.) was dissolved in dry dichloromethane (8.9 mL) under argon atmosphere at room temperature. Thereto, dry triethylamine (693 μL, 6.72 mmol, 2.10 eq.) and then TMSCl (894 μL, 7.04 mmol, 2.20 eq.) were added at 0° C. and the resulting mixture stirred for two hours at room temperature. Afterwards, the beforehand prepared solution of intermediate 4 was added at −40° C. and the reaction was stirred for 30 min., warmed to 0° C. and stirred for another hour. The reaction was quenched via the addition of dest. water (ca. 10 mL). After in vacuo removal of dichloromethane, the resulting aqueous suspension was mixed with ethyl acetate (ca. 50 mL). The pH of the aqueous phase was adjusted to 8.0 via the addition of solid $NaHCO_3$ and the layers were then separated. The aqueous layer was washed with ethyl acetate (20 mL, 3 times). The aqueous phase was then adjusted to pH=2.0 via the addition of aqueous concentrated HCl, before it was extracted with ethyl acetate (50 mL, 5 times). The combined organic layers were dried over $Na_2SO_4$, filtered and concentrated in vacuo. Thus, Acid 5 (1.04 g, 3.04 mmol, 95%) was obtained as colorless foam with a residual content of ethyl acetate (ca. 5 wt-%).

$^1H$ NMR ($CDCl_3$, 400 MHz): δ=9.88 (d, J=6.52 Hz, 1H), 5.49 (d, 6.52 Hz, 1H), 4.15-3.99 (m, 2H), 3.60-3.48 (m, 4H), 1.20 (t, J=7.65 Hz, 3H) ppm.

$^{13}C$ NMR ($CDCl_3$, 100 MHz): δ=173.2, 159.1, 155.7, 152.2, 134.9, 128.7-126.5 (3C), 55.8, 43.5, 42.6, 40.3, 12.0 ppm.

| | | |
|---|---|---|
| ESI-LRMS for $C_{15}H_{13}D_5N_3O_5^+$ [$MH^+$]: | calcd. | 325.2 |
| | found | 325.2. |

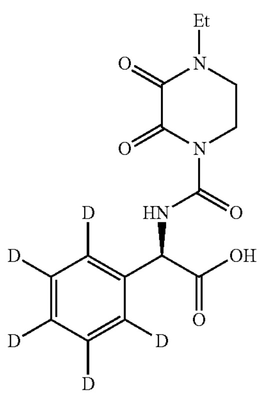

5
$C_{15}H_{12}D_5N_3O_5$
$M_w$ = 324.35

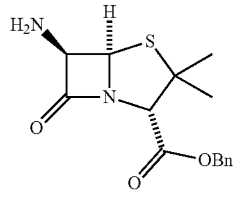

2

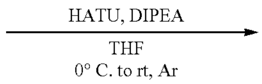

-continued

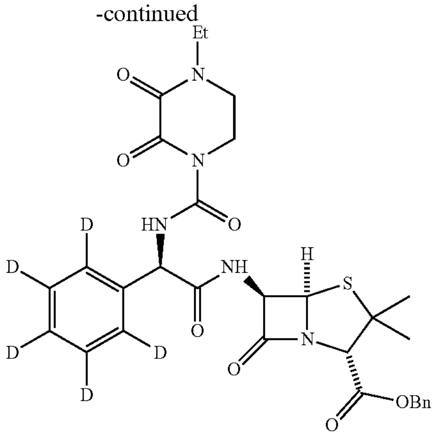

6
$C_{30}H_{28}D_5N_5O_7S$
$M_w = 612.71$

Ester (6): Acid 5 (932 mg, 2.87 mmol, 1.00 eq.) and HATU (1.26 g, 3.30 mmol, 1.15 eq.) were suspended in dry tetrahydrofuran (9.4 mL) under argon atmosphere at room temperature. After cooling to 0° C., a solution of dry DIPEA (538 μL, 3.09 mmol, 1.08 eq.) in dry tetrahydrofuran (3.0 mL) was added and the resulting mixture was stirred for 5 min. Thereafter, a solution of substance 2 (880 mg, 2.87 mmol, 1.00 eq.) in dry tetrahydrofuran (3.0 mL) was added slowly and stirring was continued at 0° C. for three hours. The reaction was quenched via addition to a stirred biphasic mixture of ethyl acetate (100 mL), aqueous phosphate buffer solution (0.2 M, pH=7.0, 40 mL) and brine (40 mL). The layers were separated and the aqueous phase was extracted with ethyl acetate (50 mL, 3 times). After combining the organic layers, drying over $Na_2SO_4$, subsequent filtration and concentration in vacuo yielded crude ester 6 as yellowish foam. Final purification was achieved via HPLC (C-18 reversed-phase silica, MeCN:$H_2O$) yielding ester 6 (1.34 g, 2.19 mmol, 76%) as colorless foam.

$^1H$ NMR ($CDCl_3$, 400 MHz): δ=9.93 (d, J=6.52 Hz, 1H), 7.40-7.32 (m, 5H), 6.46 (d, J=9.16 Hz, 1H), 5.64 (dd, J=4.02, 9.16 Hz, 1H), 5.45 (d, J=3.64 Hz, 1H), 5.44 (d, J=6.52 Hz, 1H), 5.16 (s, 2H), 4.39 (s, 1H), 4.18-4.12 (m, 1H), 3.99-3.93 (m, 1H), 3.55 (mc, 4H) 1.48 (s, 3H), 1.34 (s, 3H), 1.21 (t, J=7.63 Hz, 3H) ppm.

$^{13}C$ NMR ($CDCl_3$, 100 MHz): δ=173.3, 168.9, 167.5, 159.4, 155.8, 152.6, 136.2, 134.8, 128.9-128.8, 134.9, 127.4-126.9 (3C), 70.1, 68.2, 67.7, 64.9, 59.2, 58.9, 43.8, 42.8, 40.8, 31.8, 26.9, 12.3 ppm.

| | | |
|---|---|---|
| ESI-LRMS for $C_{30}H_{29}D_5N_5O_7S^+$ [$MH^+$]: | calcd. | 613.2 |
| | found | 613.2. |

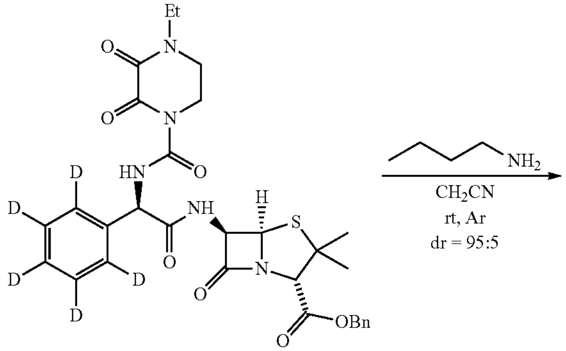

6
$C_{30}H_{28}D_5N_5O_7S$
$M_w = 612.71$

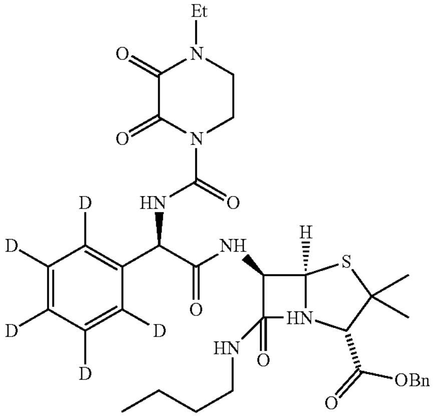

7
$C_{34}H_{39}D_5N_6O_7S$
$M_w = 685.85$

+

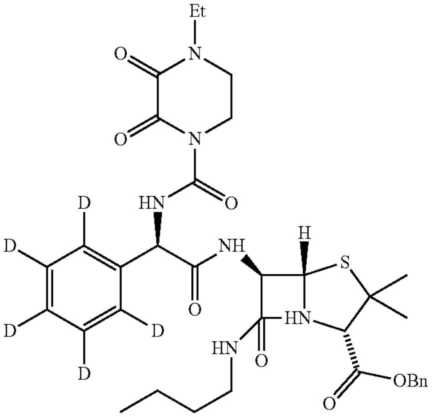

7'
$C_{34}H_{39}D_5N_6O_7S$
$M_w \approx 685.85$

Butylamide (7): Ester 6 (100 mg, 0.16 mmol, 1.00 eq.) was dissolved in dry $CH_3CN$ (2.5 mL) at room temperature under argon atmosphere. Thereto, a solution of n-butylamine (161 μL, 1.63 mmol, 10.0 eq.) in dry $CH_3CN$ (2.5 mL) was added and the resulting mixture stirred for two hours until control via LCMS indicated the complete consumption of substance 6. The reaction was quenched via addition to a stirred biphasic mixture of ethyl acetate (40 mL), aqueous phosphate buffer solution (0.2 M, pH=7.0, 10 mL) and brine (10 mL). The layers were separated and the aqueous phase was extracted with ethyl acetate (30 mL, 4 times). After combining the organic layers, drying over $Na_2SO_4$, subsequent filtration and concentration in vacuo yielded crude butylamide 7 as yellowish foam. Final purification was achieved via HPLC (C-18 reversed-phase silica, MeCN:$H_2O$, standard gradient program) yielding butylamide 7 (99.2 mg, 0.15 mmol, 89%) as colorless solid in a diastereomeric mixture of 7:7'=95:5 (determined via $^1H$ NMR).

$^1H$ NMR ($CDCl_3$, 400 MHz): δ=9.88 (d, J=7.53 Hz, 1H), 7.44-7.29 (m, 5H), 6.70-6.55 (m, 2H), 5.33 (d, J=5.90 Hz, 1H), 5.25-5.11 (m, 3H), 4.41 (dd, J=4.96, 7.53 Hz, 1H), 4.09 (ddd, J=3.64, 7.03, 13.8 Hz, 2H), 3.96 (ddd, J=3.89, 8.09, 13.8 Hz, 2H), 3.60-3.45 (m, 4H), 3.42-3.29 (m, 2H), 3.27-3.14 (m, 2H), 1.50-1.42 (m, 2H), 1.38-1.26 (m, 2H), 1.34 (s, 3H), 1.21 (t, J=7.22 Hz, 3H), 1.05 (s, 3H), 0.89 (t, J=7.34 Hz, 3H) ppm.

Characteristic signals for diastereomer 17': 6=6.78 (d, J=7.15 Hz, 1H), 6.52-6.46 (m, 1H), 5.38 (d, J=6.02 Hz, 1H), 1.12 (s, 3H) ppm. $^{13}C$ NMR ($CDCl_3$, 100 MHz): δ=169.8, 169.2, 168.8, 159.4, 155.8, 152.7, 136.2, 135.1, 128.9, 128.8, 128.8, 72.7, 67.4, 64.9, 59.6, 58.3, 57.4, 43.8, 42.8, 40.7, 39.7, 31.6, 26.4, 26.3, 20.2, 13.9, 12.3 ppm. Note: The deuterium-substituted carbon atoms could not be detected due to the line broadening, which is caused by the vicinal coupling to deuterium.

| | | |
|---|---|---|
| ESI-LRMS for $C_{34}H_{40}D_5N_6O_7S^+$ [$MH^+$]: | calcd. | 686.3 |
| | found | 686.3. |

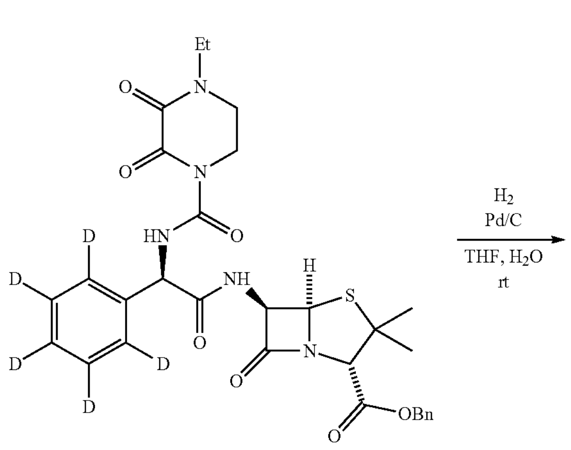

6

$C_{30}H_{28}D_5N_5O_7S$ $M_w$ = 612.71

-continued

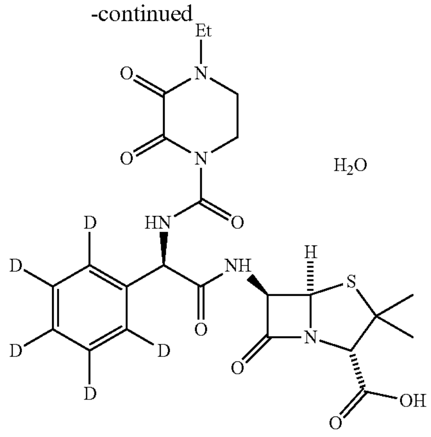

8

$C_{23}H_{24}D_5N_5O_8S$ $M_w$ = 540.60

Piperacillin-$D_5$ monohydrate (8): Ester 6 (340 mg, 0.56 mmol, 1.00 eq.) was dissolved in dry tetrahydrofuran (17 mL) at room temperature under argon atmosphere. Thereto, degassed dest. water (8.5 mL) and palladium on charcoal (10 wt-% Pd, 200 mg, 0.18 mmol, 0.33 eq. Pd) were added. Under vigorous stirring, the resulting suspension was flushed with hydrogen (1 atm, 3 times) and then hydrogenated for one hour. After filtration over a Celite plug (washings with $H_2O$:$CH_3CN$=1:1, ca. 50 mL), the resulting biphasic mixture was concentrated in vacuo (max. 30° C.) yielding a colorless foam. Thus obtained crude substance 8 was redissolved in a mixture of dest. water (3.4 mL), formic acid (105 μL, 2.78 mmol, 5.00 eq.) and acetonitrile (1.7 mL) and submitted to purification via HPLC (C-18 reversed-phase silica, MeCN:$H_2O$, standard gradient program). After concentration and thorough drying in vacuo (max. 30° C.), semi pure substance 8 (50.0 mg) was dissolved in Methanol (1.00 mL). Dest. water (1.85 mL) was added dropwise under stirring, until the mixture slowly turns turbid. After cooling to 0° C. for 30 min. further dest. water (1.00 mL) was added dropwise and the suspension was cooled to 0° C. for another 30 min. Then, the supernatant was removed from the crystals formed. After washing with ice-cold dest. water (1.00 mL, 2 times), the remaining solid was thoroughly dried in vacuo (max. 30° C.), yielding Piperacillin-$D_5$ monohydrate (8, 234 mg, 0.43 mmol, 77%) as colorless solid of 95.7% purity (determined via HPLC/UV-Vis).

$^1H$ NMR (DMSO-$D_6$, 400 MHz): δ=13.35 (br, s, 1H), 9.84 (d, J=7.28 Hz, 1H), 9.31 (d, J=7.78 Hz, 1H), 5.71 (d, J=7.28 Hz, 1H), 5.53 (dd, J=5.53, 7.78 Hz, 1H), 5.38 (d, J=4.14 Hz, 1H), 4.19 (s, 1H), 3.89 (mc, 2H), 3.56 (t, J=5.53 Hz, 2H), 3.39 (q, J=7.07 Hz, 2H), 1.54 (s, 3H), 1.39 (s, 3H), 1.08 (t, J=7.07 Hz, 3H) ppm.

$^{13}C$ NMR ($CDCl_3$, 100 MHz): δ=173.2, 169.4, 168.9, 159.5, 155.4, 151.9, 137.7, 70.3, 67.0, 63.7, 58.1, 56.5, 42.8, 41.6, 30.2, 26.6, 16.0, 11.9 ppm. Note: The deuterium-substituted carbon atoms could not be detected due to the line broadening, which is caused by the vicinal coupling to deuterium.

| | | |
|---|---|---|
| ESI-LRMS for $C_{23}H_{23}D_5N_5O_7S^+$ [$MH^+$]: | calcd. | 523.2 |
| | found | 523.2. |

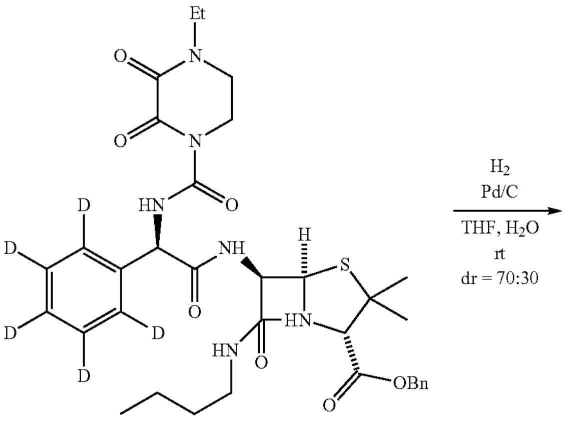

7

$C_{34}H_{39}D_5N_6O_7S$ $M_w$ = 685.85

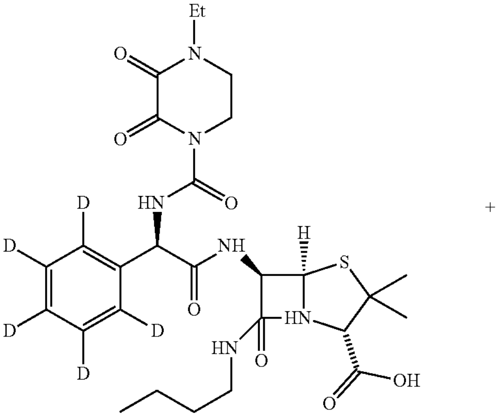

9

$C_{27}H_{33}D_5N_6O_7S$ $M_w$ = 595.73

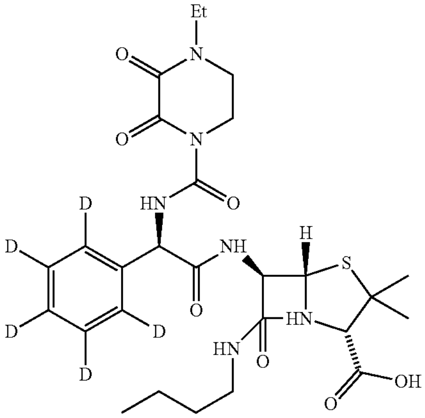

9'

$C_{27}H_{32}D_5N_6O_7S$ $M_w$ = 595.73

Piperacillin-n-butylamide-$D_5$ (9): Butylamide 7 (95.0 mg, 0.14 mmol, 1.00 eq.) was dissolved in dry tetrahydrofuran (4.0 mL) at room temperature under argon atmosphere. Thereto, degassed dest. water (2.0 mL) and palladium on charcoal (10 wt-% Pd, 74.2 mg, 0.07 mmol, 0.50 eq. Pd) were added. Under vigorous stirring, the resulting suspension was flushed with hydrogen (1 atm, 3 times) and then hydrogenated for one hour. After filtration over a Celite plug (washings with $H_2O$:$CH_3CN$=1:1, ca. 25 mL), the resulting biphasic mixture was concentrated in vacuo (max. 30° C.) yielding a colorless foam. Thus obtained crude substance 9 was redissolved in a mixture of dest. water (0.5 mL), formic acid (26.2 μL, 0.70 mmol, 5.00 eq.) and acetonitrile (1.0 mL) and submitted to purification via HPLC (C-18 reversed-phase silica, MeCN:$H_2O$). After concentration and thorough drying in vacuo (max. 30° C.), Piperacillin-n-butylamide-$D_5$ (9, 52.4 mg, 0.08 mmol, 63%) was obtained as colorless solid of 95.8% purity (determined via HPLC/UV-Vis) in a diastereomeric mixture of 9:9'=70:30 (determined via HPLC/UV-Vis).

$^1$H NMR (DMSO-$D_6$, 400 MHz): δ=12.86 (br, s, 1H, 19+19'), 9.84 (d, J=7.53 Hz, 1H, 19'), 9.84 (d, J=7.53 Hz, 1H, 19), 8.84 (d, J=8.78 Hz, 1H, 19'), 8.72 (d, J=9.03 Hz, 1H, 19), 8.18 (t, J=6.02 Hz, 1H, 19'), 8.02 (t, J=5.77 Hz, 1H, 19), 5.72 (d, J=7.53 Hz, 1H, 19+19'), 4.84 (d, J=6.40 Hz, 1H, 9), 4.71 (br, d, J=5.90 Hz, 1H, 19'), 4.63 (dd, J=6.40, 8.78 Hz, 1H, 19'), 4.34 (dd, J=7.03, 9.03 Hz, 1H, 19'), 3.92-3.87 (m, 2H, 19+19'), 3.57-3.53 (m, 2H, 19+19'), 3.44-3.36 (m, 4H, 19+19'), 3.16-2.95 (m, 2H, 19+19'), 1.48 (s, 3H, 19'), 1.40-1.23 (m, 4H, 19+19'), 1.30 (s, 3H, 19), 1.10 (s, 3H, 19), 1.08 (t, J=7.40 Hz, 1H, 19+19'), 0.93 (s, 3H, 19'), 0.86 (t, J=7.22 Hz, 1H, 19+19') ppm.

| | | |
|---|---|---|
| ESI-LRMS for $C_{27}H_{34}D_5N_6O_7S^+$ [$MH^+$]: | calcd. | 596.3 |
| | found | 596.3. |

Example 3: Synthesis of Meropenem-13C2-15N1 Trihydrate (7), Meropenem-13C2-15N-n-Butylamide (8) (Schematic Drawing and Compound Numbering See FIG. 7)

All reactions were magnetically stirred and carried out under a positive pressure of inert gas ($N_2$ or argon) utilizing standard Schlenk-techniques. Glassware was dried repeatedly at 620° C. in vacuo prior to use. Liquid reagents and solvents were added by syringes or oven-dried stainless steel cannulas through rubber septa. Solids were added under inert gas counter flow or were dissolved in appropriate solvents. Low-temperature reactions were carried out in a Dewar vessel filled with a cooling agent: acetone/dry ice (−78° C.) or $H_2O$/ice (0° C.). Reaction temperatures above room temperature were conducted in a heated oil bath. If literature-known procedures were followed, the respective reference was added to the experimental details. Yields refer to isolated homogenous and spectroscopically pure materials, if not indicated otherwise.

Solvents and Reagents: Dry solvents, such as dichloromethane ($CH_2Cl_2$), tetrahydrofuran (THF) and acetonitrile (MeCN) were purchased from commercial suppliers and used as received. Solvents for extraction and flash column chromatography were purchased in HPLC grade. All other reagents and solvents were purchased from chemical suppliers (Sigma-Aldrich, Acros Organics, Alfa Aesar, TCI Europe, abcr) and were used as received.

[1]: trans-4-Hydroxy-L-proline (S1, 1.0 g, 7.6 mmol, 1.0 eq.) was dissolved in aqueous NaOH (0.5 M, 34 mL) and cooled in an ice bath. At 0-5° C., 4-nitrobenzoylchloroformate (1.9 g, 8.6 mmol, 1.1 eq.) in toluene (25 mL) was added dropwise. The bi-phasic mixture was stirred fortwo hours, after which the toluene (30 mL) was added and the phases separated.

The aqueous phase was extracted with toluene and the combined organic phases extracted with aqueous NaOH (0.5

M). The aqueous phases were combined, adjusted to pH=1 by adding conc. HCl and extracted with ethyl acetate (3 times). The extract was dried over sodium sulfate, filtered and concentrated in vacuo. Thus, compound 1 (1.89 g, 6.1 mmol, 80%) was obtained as off-white solid.

| | | |
|---|---|---|
| ESI-LRMS for $C_{13}H_{15}N_2O_7^+$ [MH$^+$]: | calcd. | 311.1 |
| | found | 311.2 |

[2]: Substance 1 (1.4 g, 4.5 mmol, 1.0 eq.) was dissolved in acetonitrile (70 mL) and 1.7 g HBTU (1.7 g, 4.5 mmol, 1.0 eq.), 416 mg Dimethylamine-$^{13}C_2$-$^{15}N$ hydrochloride (0.4 g, 5.1 mmol, 1.1 eq.) under argon atmosphere at room temperature and 2.6 mL triethylamine (2.6 mL, 19 mmol, 4.2 eq.) were added sequentially. This mixture was stirred for 90 minutes. Then the acetonitrile was evaporated. The crude product was suspended in ethyl acetate (20 mL) and filtered. The filtrate was washed with sat. bicarbonate solution several times. The ethyl acetate was evaporated and the resulting solid stored at −20° C. The product was suspended in ethyl acetate (20 mL) again and filtered. The filtrate was concentrated to 10 mL volume and the solution cooled to 0° C. The precipitate formed was filtered off and dried in vacuo, yielding substance 2 (1.27 g, 3.7 mmol, 83%) as off-white solid.

| | | |
|---|---|---|
| ESI-LRMS for $C_{13}{}^{13}C_2H_{20}N_2{}^{15}NO_6^+$ [MH$^+$]: | calcd. | 341.3 |
| | found | 341.1 |

[3]: Substance 2 (1.16 g, 3.41 mmol, 1.00 eq.) was dried in vacuo and dissolved in anhydrous pyridine (9.0 mL) under argon atmosphere. Methanesulfonyl chloride (0.53 mL, 6.82 mmol, 2.00 eq.) was added and the resulting mixture stirred for 45 min at room temperature. The pyridine was removed in vacuo and ethyl acetate (200 mL) and sat. aqueous bicarbonate solution (100 mL) were added. The layers were mixed, separated and the organic phase extracted with sat. aqueous bicarbonate solution (100 mL). The organic phase was dried over sodium sulfate, filtered and concentrated in vacuo, yielding substance 3 (1.44 g, 3.4 mmol, 99%) as off-white solid.

| | | |
|---|---|---|
| ESI-LRMS for $C_{14}{}^{13}C_2H_{22}N_2{}^{15}NO_8S^+$ [MH$^+$]: | calcd. | 419.4 |
| | found | 419.3 |

[4]: Substance 3 (1.42 g, 3.39 mmol, 1.00 eq.) was dried in vacuo and transferred with anhydrous DMF (23 mL) to a flame dried pressure tube under argon atmosphere. 775 mg Potassium thioacetate (0.78 g, 6.78 mmol, 2.00 eq.) was added and the resulting mixture heated to 70° C. for one hour. The reaction was monitored by HPLC and the addition of additional amounts of potassium thioacetate (0.78 g, 6.78 mmol, 2.00 eq.) and heating repeated until >95% of starting material were consumed. The pyridine was removed in vacuo and ethyl acetate (200 mL) were added. The resulting suspension was washed with dest. water (100 mL) and brine (100 mL). The organic layer was dried over sodium sulfate, filtered and concentrated in vacuo, yielding substance 4 (1.19 g, 3.0 mmol, 88%) as “colorless solid”.

| | | |
|---|---|---|
| ESI-LRMS for $C_{15}{}^{13}C_2H_{22}N_2{}^{15}NO_6S^+$ [MH$^+$]: | calcd. | 399.4 |
| | found | 399.5 |

[5]: Substance 4 (1.12 g, 2.81 mmol, 1.00 eq.) was dissolved in MeOH (47 mL) and cooled to 0° C. Aqueous NaOH (1 M, 2.7 mL) was added and the reaction mixture stirred for three hours. Then, the mixture was acidified to pH=2 by adding aqueous HCl (0.5 M) and the methanol removed in vacuo. The residue was dissolved in ethyl acetate (350 mL), the layers were separated and the organic layer was washed with brine (100 mL). The organic phase was dried over sodium sulfate, filtered and concentrated in vacuo. The crude product was purified via HPLC (C-18 reversed-phase silica, MeCN:$H_2O$). Thus compound 5 (0.45 g, 1.26 mmol, 45%) was isolated as colorless solid.

| | | |
|---|---|---|
| ESI-LRMS for $C_{13}{}^{13}C_2H_{19}N_2{}^{15}NO_5S^+$ [MH$^+$]: | calcd. | 356.4 |
| | found | 356.5 |

[6]: Hydration buffer for the synthesis of substance 7: N-Methylmorpholine (720 μL) and acetic acid (360 μL) were added to dest. water (19.0 mL) and the pH adjusted to 6 via addition of acetic acid.

[7](Meropenem-$^{13}C_2$-$^{15}N$ trihydrate): Substance 5 (0.48 g, 1.36 mmol, 1.00 eq.) was dissolved in a mixture of ethyl acetate (15 mL) and DMF (3.0 mL). The resulting solution was cooled to <5° C. Then, compound S2 (0.89 g, 1.50 mmol, 1.10 eq.) and DIPA (0.26 mL, 1.86 mmol, 1.36 eq.) were added dropwise. Thereafter, the mixture was stirred for 3.5 hours at 0-5° C. The reaction was monitored by HPLC. Upon full conversion of substance 5, hydration buffer (12 mL) was added to the reaction mixture. The mixture was stirred for three hours and then transferred to a hydration apparatus. Palladium on charcoal (10 wt-% Pd, 0.74 g, 0.69 mmol, 0.50 eq. Pd) was added and the reaction vessel purged with hydrogen (4.8 bar). The reaction mixture was hydrogenated for three hours. Thereafter, the organic layer was separated and the catalyst removed by filtration. The crude product was purified via HPLC (C-18 reversed-phase silica, MeCN:$H_2O$). Thus compound 5 (71.9 mg, 0.16 mmol, 12%) was isolated as colorless solid.

| | | |
|---|---|---|
| ESI-LRMS for $C_{15}{}^{13}C_2H_{26}N_2{}^{15}NO_5S^+$ [MH$^+$]: | calcd. | 387.4 |
| | found | 387.3 |

[8] Meropenem-Butylamide-$^{13}C_2$-$^{15}N$: Meropenem-$^{13}C_2$-$^{15}N$ trihydrate (7, 50 mg, 0.13 mmol, 1.0 eq.) was dissolved in water (0.5 mL) under argon atmosphere at room temperature. n-butylamine (4.5 M, 0.12 mL, 0.5 mmol, 3.8 eq.) was added and the resulting mixture was stirred for 30 minutes. Afterwards, the reaction was lyophilized. The residual solid was purified via HPLC (C-18 reversed-phase silica, MeCN:$H_2O$). Thus compound 8 (40 mg, 0.08 mmol, 67%) was obtained as off-white solid.

| | | |
|---|---|---|
| ESI-LRMS for $C_{19}{}^{13}C_2H_{37}N_5{}^{15}NO_5S^+$ [MH$^+$]: | calcd. | 460.3 |
| | found | 460.2 |

[9] Butylamide: Ester 6 (100 mg, 0.29 mmol, 1.00 eq.) was dissolved in dry $CH_3CN$ (4.0 mL) at room temperature under argon atmosphere. Thereto, a solution of n-butylamine (282 μL, 2.85 mmol, 10.0 eq.) in dry $CH_3CN$ (2.5 mL) was added and the resulting mixture stirred for two hours until control via LCMS indicated the complete consumption of substance 6. The reaction was quenched via addition to a stirred biphasic mixture of ethyl acetate (60 mL), aqueous phosphate buffer solution (0.2 M, pH=7.0, 20 mL) and brine (20 mL). The layers were separated and the aqueous phase was extracted with ethyl acetate (30 mL, 3 times). After combining the organic layers and drying over $Na_2SO_4$, subsequent filtration and concentration in vacuo yielded crude butylamide 9 as brownish foam. Final purification was achieved via HPLC (C-18 reversed-phase silica, MeCN: $H_2O$) yielding butylamide 9 (164 mg, 0.21 mmol, 73%) as colorless foam in a diastereomeric mixture.

| | | |
|---|---|---|
| ESI-LRMS for $C_{34}{}^{13}C_2H_{47}N_5{}^{15}NO_{11}S^+$ [$MH^+$]: | calcd. | 774.3 |
| | found | 774.3 |

[10] Meropenem-Butylamide-$^{13}C_2$-$^{15}N$: Butylamide 9 (100 mg, 0.13 mmol, 1.00 eq.) was dissolved in dry tetrahydrofuran (4.0 mL) at room temperature under argon atmosphere. Thereto, degassed dest. water (2.0 mL) and palladium on charcoal (10 wt-% Pd, 68.9 mg, 0.07 mmol, 0.50 eq. Pd) were added. Under vigorous stirring, the resulting suspension was flushed with hydrogen (1 atm, 3 times) and then hydrogenated for three hours. After filtration over a Celite plug (washings with $H_2O$:$CH_3CN$=1:1, ca. 25 mL), the resulting biphasic mixture was concentrated in vacuo (max. 30° C.) yielding a yellowish foam. Thus obtained crude substance 8 was redissolved in a mixture of dest. water (0.8 mL), formic acid (15.7 μL, 0.42 mmol, 3.00 eq.), and acetonitrile (0.8 mL) and submitted to purification via HPLC (C-18 reversed-phase silica, MeCN:$H_2O$). After concentration and thorough drying in vacuo (max. 30° C.), Meropenem-Butylamide-$^{13}C_2$-$^{15}N$ (8, 23.3 mg, 0.05 mmol, 39%) was obtained as slightly yellowish solid in a diastereomeric mixture of superior purity.

| | | |
|---|---|---|
| ESI-LRMS for $C_{19}{}^{13}C_2H_{37}N_3{}^{15}NO_5S^+$ [$MH^+$]: | calcd. | 460.3 |
| | found | 460.2 |

Example 4: Stability of Derivatized Piperacillin

To assess whether full β-Lactam derivatization is achievable using simple propylamine, butylamine or pentylamine, these nucleophiles were added in high excess to solutions of Meropenem (compound 1, FIG. 3) and Piperacillin (compound 5, FIG. 1 or 4, 1 μg/mL).

For schematic drawing of the chemical reactions, see FIGS. 3 and 4, for Meropenem and Piperacillin, respectively.

The stability of double butylamide variants of Piperacillin (compound 7, see FIG. 4) was investigated at 2 MRMs using the identical protocol as in Examples 1.

Figure 5:
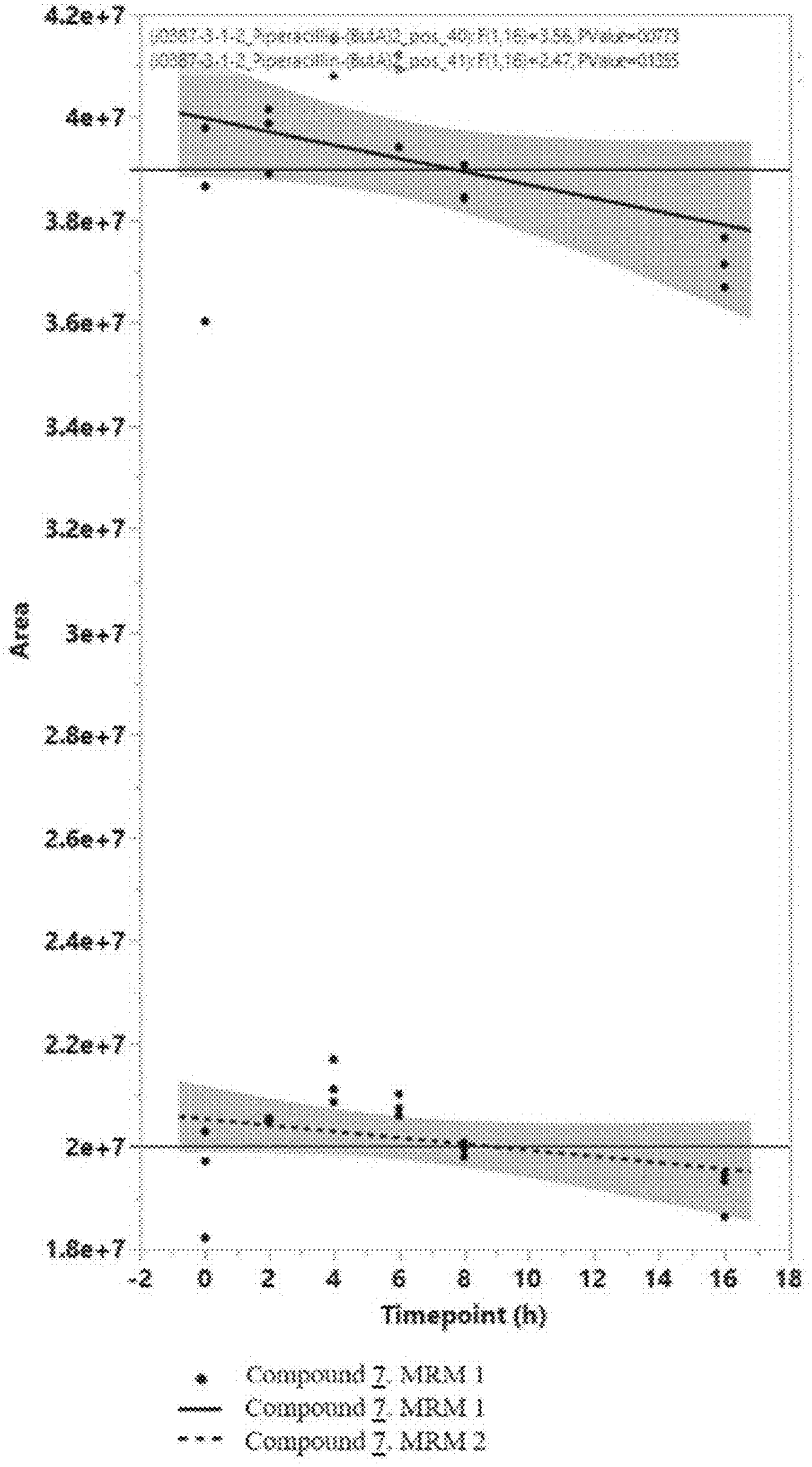

FIG. 5 shows the obtained areas for two MRM transitions for compound 7. It is observed that the obtained peak-areas do not vary significantly over time, i.e. the derivatized Piperacillin does not hydrolyse. This is further corroborated by an F-test, yielding P values of 0.08 and 0.14.

Example 5: Stabilization of Meropenem (Compound 1) and Piperacillin (Compound 5) in Patient Samples Derivatization reagents (propylamine, butylamine, or pentylamine), dissolved in water were added to 100 μL of sample (serum spiked with 1 μg/mL of both Piperacillin (compound 5) and Meropenem (compound 1)).

Relative to 100 μL of a 1 μg/mL ($1.9*10^{-9}$ M) Piperacillin (compound 5), $5*10^8$, $2.5*10^8$ or $2.5*10^6$ equivalents ($9.8*10^{-5}$, $4.8*10^{-5}$, $1.9*10^{-7}$ moles respectively) of the respective derivatization reagents (20 μL) were added to the spiked serum. This mixture was then incubated for 3 minutes after which a pH adjustment reagent (40 μL of an aqueous 1 M HCOOH (pH 2.5) or 500 mM $Na_3PO_4$/$Na_2HPO_4$ (pH 12)) was added. Subsequently, magnetic beads (40 μL, 50 mg/mL) were added and incubated for 3 minutes. The supernatant was next removed and the beads were washed twice with water (150 μL). Next, an elution solution (50 μL of a solution with either 100 mM HCOOH, 100 mM pyrrolidin or no pH adjustment reagent in varying levels of acetonitrile (10-90%, v/v) was added. The supernatant (20 μL) was next diluted with water (20 μL).

To quantify both the native (intact) Meropenem (compound 1) and Piperacillin (compound 5), as well as their derivatized products and the hydrolyzed compounds, a LC-MS/MS method was devised including tuned MRM transitions for all compounds. A Cortecs C18+C18, 2.6 μm, 2.1 mm×50 mm column with Solvent A: water with 0.1% HCOOH and Solvent B: $CH_3CN$ with 0.1% HCOOH and a flow of 0.6 mL per minute on an Agilent Infinity II multisampler/Pump system connected to an AB Sciex 6500+MS. For each of the derivatized antibiotics (i.e. Meropenem (a386) and Piperacillin (a0387), derivatized with either propylamine, butylamine or amylamine), three MRM transitions were used. Native Meropenem (compound 1) and Piperacillin (compound 5), as well as their hydrolyzed forms (2 MRM transitions per analyte) were also included in the measurement.

| Name | Q 1 Mass (Da) | Q 3 Mass (Da) | Time (min) | DP (volts) | CE (volts) | CXP (volts) |
|---|---|---|---|---|---|---|
| a0386_Meropenem | 384.1 | 141 | 1.8 | 96 | 23 | 12 |
| a0387_Piperacillin_1 | 540.2 | 398 | 3.2 | 1 | 25 | 14 |
| a0386_PropA_pos1 | 443 | 181 | 1.7 | 31 | 31 | 6 |
| a0386_PropA_pos2 | 443 | 173 | 1.7 | 31 | 27 | 10 |
| a0386_PropA_pos3 | 443 | 399 | 1.7 | 26 | 15 | 20 |
| a0386_ButA_pos1 | 457.2 | 413.2 | 1.7 | 51 | 13 | 24 |
| a0386_ButA_pos2 | 457.2 | 195.2 | 1.7 | 51 | 25 | 16 |
| a0386_ButA_pos3 | 457.2 | 175.1 | 1.7 | 51 | 23 | 10 |
| a0386_PentA_pos1 | 471.2 | 427.2 | 1.7 | 56 | 15 | 20 |
| a0386_PentA_pos2 | 471.2 | 209.2 | 1.7 | 56 | 25 | 14 |
| a0386_PentA_pos3 | 471.2 | 175.1 | 1.7 | 56 | 25 | 10 |
| a0387_PropA_pos1 | 636.2 | 477.2 | 3.3 | 106 | 23 | 22 |
| a0387_PropA_pos2 | 636.2 | 361.2 | 3.3 | 106 | 27 | 16 |
| a0387_PropA_pos3 | 636.2 | 205 | 3.3 | 106 | 63 | 6 |
| a0387_ButA_pos1 | 664.2 | 375.1 | 3.3 | 126 | 27 | 24 |
| a0387_ButA_pos2 | 664.2 | 505.2 | 3.3 | 126 | 23 | 30 |
| a0387_ButA_pos3 | 664.2 | 106.1 | 3.3 | 126 | 39 | 14 |
| a0387_PentA_pos1 | 692.4 | 389.2 | 4.2 | 131 | 27 | 22 |
| a0387_PentA_pos2 | 692.4 | 533.3 | 4.2 | 131 | 25 | 28 |
| a0387_PentA_pos3 | 692.4 | 278.1 | 4.2 | 131 | 33 | 18 |
| a0386_Hydrolyzed Meropenem_Neg_1 | 399.8 | 152 | 1.8 | −60 | −24 | −5 |
| a0386_Hydrolyzed Meropenem_Neg_2 | 399.8 | 173 | 1.8 | −60 | −34 | −13 |
| a0387_Hydrolyzed Piperacillin_Neg_1 | 551.9 | 270 | 1.8 | −30 | −34 | −15 |
| a0387_Hydrolyzed Piperacillin_Neg_2 | 551.9 | 464 | 1.8 | −30 | −22 | −21 |

For Meropenem (compound 1), the results with the highest peak-areas are obtained when using pentylamine. At a concentration of 1 μg/mL in serum of this antibiotic, using pentylamine and an optimal workflow, an area of about 3E6 should be possible. Using butylamine, under optimal conditions areas of 1E6 are achievable. See FIG. 6.

For Piperacillin (compound 5) the results with the highest peak-areas are obtained when using butylamine. At a concentration of 1 μg/mL in serum of this antibiotic, using butylamine and an optimal workflow (see next section for optimal workflows), an area of 2E7 should be possible. See FIG. 7.

It is noted that no residual native compound (intact Meropenem (compound 1) or Piperacillin (compound 5)) is found in the eluate, when using 2.5E8 equivalents of the reagent. This shows that the reaction in this short time is quantitative. Furthermore, we observe no increase in the amount of hydrolyzed compound, indicating that the addition of the nucleophile does not catalyze hydrolyzation of the lactam moiety in these compounds, making it possible to discriminate and quantify the intact lactam compound from the hydrolyzed compound.

This patent application claims the priority of the European patent application 19209520.6, wherein the content of this European patent application is hereby incorporated by references.

The invention claimed is:

1. A complex formed of an antibiotic substance and a nucleophilic derivatization reagent, the complex including an isotopic label, wherein the nucleophilic derivatization reagent is a linear primary amine comprising a primary amine group and in the range of from 3 to 10 C-atoms, and wherein the antibiotic substance is a beta-lactam antibiotic.

2. The complex of claim 1, wherein the antibiotic substance is Meropenem or Piperacillin.

3. A composition comprising the complex of claim 1.

4. A composition comprising the complex of claim 1, wherein the composition further comprises a solvent.

5. The composition of claim 4, further comprising a non-nucleophilic base that is stable and miscible with water.

6. A kit comprising a) the complex of claim 1, and b) a package insert.

7. A derivatized beta-lactam antibiotic substance comprising an isotopic label, derivatized with a nucleophilic derivatization reagent, wherein the nucleophilic derivatization reagent is a linear primary amine comprising a primary amine group and in the range of from 3 to 10 C-atoms, the derivatized beta-lactam antibiotic substance being suitable as an internal standard (ISTD) and/or a calibrator in Mass Spectrometry Measurements.

8. A method of producing a stabilized antibiotic substance, comprising derivatizing a beta-lactam antibiotic substance with a nucleophilic derivatization reagent to stabilize the antibiotic substance, wherein the nucleophilic derivatization reagent is a linear primary amine comprising a primary amine group and in the range of from 3 to 10 C-atoms, wherein the antibiotic substance and/or the nucleophilic derivatization reagent comprises one or more isotopic label.

9. The composition of claim 4, wherein the solvent is selected from the group consisting of water, $CH_3CN$, THF, Dioxanes, DMF, DMSO, acetone, t-butyl alcohol, diglyme, DME, MeOH, EtOH, 1-PrOH, 2-PrOH, ethylene glycol, Hexamethylphosphoramiede (HMPA), Hexamethylphosphorous triamide (HMPT), and glycerin.

10. The composition of claim 5, wherein the non-nucleophilic base is selected from the group consisting of DBU, $Na_3PO_4$, $Na_2CO_3$, and $Cs_2CO_3$.

11. The method of claim 8, wherein the antibiotic substance is Meropenem or Piperacillin.

12. The method of claim 8, wherein the nucleophilic derivatization reagent stabilizes the antibiotic substance by preventing hydrolyzation of the antibiotic substance.

13. The method of claim 8, wherein the nucleophilic derivatization reagent stabilizes the antibiotic substance for more than 12 hours.

14. The method of claim 8, wherein the nucleophilic derivatization reagent is provided in an excess of from about 1E5 to about 1E10 compared to the amount of antibiotic substance present.

15. The method of claim 8, wherein the derivatized antibiotic substance is used as an internal standard (ISTD) and/or a calibrator in Mass Spectrometry Measurements.

16. The complex of claim 1, wherein the complex comprises one or more isotopic label(s) in the antibiotic substance of the complex.

17. The complex of claim 1, wherein the complex comprises 1 to 10 isotopic label(s) in the antibiotic substance of the complex.

* * * * *